US011636944B2

(12) United States Patent
Hanrahan et al.

(10) Patent No.: US 11,636,944 B2
(45) Date of Patent: Apr. 25, 2023

(54) CONNECTIVITY INFRASTRUCTURE FOR A TELEHEALTH PLATFORM

(71) Applicant: INTOUCH TECHNOLOGIES, INC., Goleta, CA (US)

(72) Inventors: Kevin Hanrahan, Santa Barbara, CA (US); John Schentrup, Lompoc, CA (US); Parixit Kaira, Santa Barbara, CA (US); Marco Pinter, Santa Barbara, CA (US); John Cody Herzog, Santa Barbara, CA (US); Blair Whitney, Santa Barbara, CA (US); Jonathan Southard, Santa Barbara, CA (US)

(73) Assignee: TELADOC HEALTH, INC., Purchase, NY (US)

( * ) Notice: Subject to any disclaimer, the term of this patent is extended or adjusted under 35 U.S.C. 154(b) by 1185 days.

(21) Appl. No.: 16/114,091

(22) Filed: Aug. 27, 2018

(65) Prior Publication Data
US 2019/0066837 A1 Feb. 28, 2019

Related U.S. Application Data

(60) Provisional application No. 62/550,514, filed on Aug. 25, 2017.

(51) Int. Cl.
*G16H 40/20* (2018.01)
*G16H 10/60* (2018.01)
(Continued)

(52) U.S. Cl.
CPC ........... *G16H 40/20* (2018.01); *A61B 5/0002* (2013.01); *G06F 11/3055* (2013.01);
(Continued)

(58) Field of Classification Search
CPC .... G06F 11/3055; G16H 40/20; G16H 80/00; H04L 67/24
(Continued)

(56) References Cited

U.S. PATENT DOCUMENTS 3,821,995 A 7/1974 Aghnides
4,107,689 A 8/1978 Jellinek
(Continued)

FOREIGN PATENT DOCUMENTS

AU 1216200 A 5/2000
CA 2289697 A1 11/1998
(Continued)

OTHER PUBLICATIONS

Ilias Maglogiannis;Enabling Collaborative Medical Diagnosis Over the Internet via Peer-to-Peer Distribution of Electronic Health Records; May 26, 2005 / Accepted: Jun. 30, 2005, Springer Science+Business Media, Inc. 2006 (Year: 2006).*
(Continued)

*Primary Examiner* — Hiep V Nguyen (57) ABSTRACT

A secure, reliable telehealth delivery platform that also provides flexibility and scalability. The platform includes a plurality of geographically dispersed communication servers that facilitate communication sessions between remotely located patients and healthcare providers over a public communications network. The platform includes a connectivity server that manages access among users and locations. The platform also includes a monitoring server that monitors the health and usage of devices coupled to the network and proactively identifies issues requiring intervention before service interruptions occur.

17 Claims, 2 Drawing Sheets

(51) Int. Cl.
  *A61B 5/00* (2006.01)
  *G16H 50/30* (2018.01)
  *G16H 50/20* (2018.01)
  *G16H 80/00* (2018.01)
  *G06F 11/30* (2006.01)
  *H04L 67/54* (2022.01)

(52) U.S. Cl.
  CPC ............ *G16H 10/60* (2018.01); *G16H 50/20* (2018.01); *G16H 50/30* (2018.01); *G16H 80/00* (2018.01); *H04L 67/54* (2022.05)

(58) Field of Classification Search
  USPC .......................................................... 705/2
  See application file for complete search history.

(56) References Cited

U.S. PATENT DOCUMENTS

| | | |
|---|---|---|
| 4,213,182 A | 7/1980 | Eichelberger et al. |
| 4,413,693 A | 11/1983 | Derby |
| 4,471,354 A | 9/1984 | Smith |
| 4,519,466 A | 5/1985 | Shiraishi |
| 4,553,309 A | 11/1985 | Hess et al. |
| 4,572,594 A | 2/1986 | Schwartz |
| 4,625,274 A | 11/1986 | Schroeder |
| 4,638,445 A | 1/1987 | Mattaboni |
| 4,652,204 A | 3/1987 | Arnett |
| 4,669,168 A | 6/1987 | Tamura et al. |
| 4,679,152 A | 7/1987 | Perdue |
| 4,697,278 A | 9/1987 | Fleischer |
| 4,697,472 A | 10/1987 | Hiyane |
| 4,709,265 A | 11/1987 | Silverman et al. |
| 4,733,737 A | 3/1988 | Falamak |
| 4,751,658 A | 6/1988 | Kadonoff et al. |
| 4,766,581 A | 8/1988 | Korn et al. |
| 4,777,416 A | 10/1988 | Georg et al. |
| 4,797,557 A | 1/1989 | Ohman |
| 4,803,625 A | 2/1989 | Fu et al. |
| 4,847,764 A | 7/1989 | Halvorson |
| 4,875,172 A | 10/1989 | Kanayama |
| 4,878,501 A | 11/1989 | Shue |
| 4,942,512 A | 7/1990 | Kohno |
| 4,942,538 A | 7/1990 | Yuan et al. |
| 4,953,159 A | 8/1990 | Hayden et al. |
| 4,974,607 A | 12/1990 | Miwa |
| 4,977,971 A | 12/1990 | Cran et al. |
| 5,006,988 A | 4/1991 | Borenstein et al. |
| 5,040,116 A | 8/1991 | Evans, Jr. et al. |
| 5,051,906 A | 9/1991 | Evans, Jr. et al. |
| 5,073,749 A | 12/1991 | Kanayama |
| 5,084,828 A | 1/1992 | Kaufman et al. |
| 5,130,794 A | 7/1992 | Ritchey |
| 5,148,591 A | 9/1992 | Pryor |
| 5,153,833 A | 10/1992 | Gordon et al. |
| 5,155,684 A | 10/1992 | Burke et al. |
| 5,157,491 A | 10/1992 | Kassatly |
| 5,182,641 A | 1/1993 | Diner et al. |
| 5,186,270 A | 2/1993 | West |
| 5,193,143 A | 3/1993 | Kaemmerer et al. |
| 5,217,453 A | 6/1993 | Wilk |
| 5,220,263 A | 6/1993 | Onishi et al. |
| 5,224,157 A | 6/1993 | Yamada et al. |
| 5,230,023 A | 7/1993 | Nakano |
| 5,231,693 A | 7/1993 | Backes et al. |
| 5,236,432 A | 8/1993 | Matse et al. |
| 5,262,944 A | 11/1993 | Weisner et al. |
| 5,305,427 A | 4/1994 | Nagata |
| 5,315,287 A | 5/1994 | Sol |
| 5,319,611 A | 6/1994 | Korba |
| 5,341,242 A | 8/1994 | Gilboa et al. |
| 5,341,459 A | 8/1994 | Backes |
| 5,341,854 A | 8/1994 | Zezulka et al. |
| 5,347,306 A | 9/1994 | Nitta |
| 5,347,457 A | 9/1994 | Tanaka et al. |
| 5,350,033 A | 9/1994 | Kraft |
| 5,366,896 A | 11/1994 | Margrey et al. |
| 5,374,879 A | 12/1994 | Pin et al. |
| 5,375,195 A | 12/1994 | Johnston |
| 5,400,068 A | 3/1995 | Ishida et al. |
| 5,417,210 A | 5/1995 | Funda et al. |
| 5,419,008 A | 5/1995 | West |
| 5,436,542 A | 7/1995 | Petelin et al. |
| 5,441,042 A | 8/1995 | Putman |
| 5,441,047 A | 8/1995 | David et al. |
| 5,442,728 A | 8/1995 | Kaufman et al. |
| 5,462,051 A | 10/1995 | Oka et al. |
| 5,486,853 A | 1/1996 | Baxter et al. |
| 5,510,832 A | 4/1996 | Garcia |
| 5,511,147 A | 4/1996 | Abdel-Malek |
| 5,528,289 A | 6/1996 | Cortjens et al. |
| 5,539,741 A | 7/1996 | Barraclough et al. |
| 5,544,649 A | 8/1996 | David et al. |
| 5,550,577 A | 8/1996 | Verbiest et al. |
| 5,553,609 A | 9/1996 | Chen et al. |
| 5,563,998 A | 10/1996 | Yaksich et al. |
| 5,572,229 A | 11/1996 | Fisher |
| 5,572,999 A | 11/1996 | Funda et al. |
| 5,594,859 A | 1/1997 | Palmer et al. |
| 5,600,573 A | 2/1997 | Hendricks et al. |
| 5,617,539 A | 4/1997 | Ludwig et al. |
| 5,619,341 A | 4/1997 | Auyeung et al. |
| 5,623,679 A | 4/1997 | Rivette et al. |
| 5,630,566 A | 5/1997 | Case |
| 5,636,218 A | 6/1997 | Ishikawa et al. |
| 5,652,849 A | 7/1997 | Conway et al. |
| 5,657,246 A | 8/1997 | Hogan et al. |
| 5,659,779 A | 8/1997 | Laird et al. |
| 5,673,082 A | 9/1997 | Wells et al. |
| 5,675,229 A | 10/1997 | Thorne |
| 5,682,199 A | 10/1997 | Lankford |
| 5,684,531 A | 11/1997 | Li et al. |
| 5,684,695 A | 11/1997 | Bauer |
| 5,701,904 A | 12/1997 | Simmons et al. |
| 5,734,805 A | 3/1998 | Isensee et al. |
| 5,739,657 A | 4/1998 | Takayama et al. |
| 5,748,629 A | 5/1998 | Caldara et al. |
| 5,749,058 A | 5/1998 | Hashimoto |
| 5,749,362 A | 5/1998 | Funda et al. |
| 5,754,631 A | 5/1998 | Cave |
| 5,758,079 A | 5/1998 | Ludwig et al. |
| 5,762,458 A | 6/1998 | Wang et al. |
| 5,764,731 A | 6/1998 | Yablon |
| 5,767,897 A | 6/1998 | Howell |
| 5,786,846 A | 7/1998 | Hiroaki |
| 5,787,545 A | 8/1998 | Colens |
| 5,793,365 A | 8/1998 | Tang et al. |
| 5,799,055 A | 8/1998 | Peshkin et al. |
| 5,801,755 A | 9/1998 | Echerer |
| 5,802,494 A | 9/1998 | Kuno |
| 5,836,872 A | 11/1998 | Kenet et al. |
| 5,838,575 A | 11/1998 | Lion |
| 5,844,599 A | 12/1998 | Hildin |
| 5,857,534 A | 1/1999 | DeVault et al. |
| 5,867,494 A | 2/1999 | Krishnaswamy et al. |
| 5,867,653 A | 2/1999 | Aras et al. |
| 5,871,451 A | 2/1999 | Unger et al. |
| 5,872,922 A | 2/1999 | Hogan et al. |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,949,758 A | 9/1999 | Kober |
| 5,954,692 A | 9/1999 | Smith et al. |
| 5,959,423 A | 9/1999 | Nakanishi et al. |
| 5,961,446 A | 10/1999 | Beller et al. |
| 5,966,130 A | 10/1999 | Benman, Jr. |
| 5,973,724 A | 10/1999 | Riddle |
| 5,974,446 A | 10/1999 | Sonnenreich et al. |
| 5,983,263 A | 11/1999 | Rothrock et al. |
| 5,995,119 A | 11/1999 | Cosatto et al. |
| 5,995,884 A | 11/1999 | Allen et al. |
| 5,999,977 A | 12/1999 | Riddle |
| 6,006,946 A | 12/1999 | Williams et al. |
| 6,031,845 A | 2/2000 | Walding |

(56) References Cited

U.S. PATENT DOCUMENTS

| | | |
|---|---|---|
| 6,036,812 A | 3/2000 | Williams et al. |
| 6,047,259 A | 4/2000 | Campbell et al. |
| 6,091,219 A | 7/2000 | Maruo et al. |
| 6,113,343 A | 9/2000 | Goldenberg et al. |
| 6,133,944 A | 10/2000 | Braun et al. |
| 6,135,228 A | 10/2000 | Asada et al. |
| 6,148,100 A | 11/2000 | Anderson et al. |
| 6,160,582 A | 12/2000 | Hill |
| 6,170,929 B1 | 1/2001 | Wilson et al. |
| 6,175,779 B1 | 1/2001 | Barrett |
| 6,189,034 B1 | 2/2001 | Riddle |
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba et al. |
| 6,233,504 B1 | 5/2001 | Das et al. |
| 6,233,735 B1 | 5/2001 | Ebihara |
| 6,250,928 B1 | 6/2001 | Poggio et al. |
| 6,256,556 B1 | 7/2001 | Zenke |
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,292,714 B1 | 9/2001 | Okabayashi |
| 6,304,050 B1 | 10/2001 | Skaar et al. |
| 6,313,853 B1 | 11/2001 | Lamontagne et al. |
| 6,314,631 B1 | 11/2001 | Pryor |
| 6,317,652 B1 | 11/2001 | Osada |
| 6,317,953 B1 | 11/2001 | Pryor |
| 6,321,137 B1 | 11/2001 | De Smet |
| 6,324,184 B1 | 11/2001 | Hou et al. |
| 6,324,443 B1 | 11/2001 | Kurakake et al. |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,331,181 B1 | 12/2001 | Tierney et al. |
| 6,346,950 B1 | 2/2002 | Jouppi |
| 6,346,962 B1 | 2/2002 | Goodridge |
| 6,369,847 B1 | 4/2002 | James et al. |
| 6,373,855 B1 | 4/2002 | Downing et al. |
| 6,381,515 B1 | 4/2002 | Inoue et al. |
| 6,389,329 B1 | 5/2002 | Colens |
| 6,400,378 B1 | 6/2002 | Snook |
| 6,408,230 B2 | 6/2002 | Wada |
| 6,411,055 B1 | 6/2002 | Fujita et al. |
| 6,430,471 B1 | 8/2002 | Kintou et al. |
| 6,430,475 B2 | 8/2002 | Okamoto et al. |
| 6,438,457 B1 | 8/2002 | Yokoo et al. |
| 6,445,964 B1 | 9/2002 | White et al. |
| 6,449,762 B1 | 9/2002 | McElvain |
| 6,452,915 B1 | 9/2002 | Jorgensen |
| 6,457,043 B1 | 9/2002 | Kwak et al. |
| 6,459,955 B1 | 10/2002 | Bartsch et al. |
| 6,463,352 B1 | 10/2002 | Tadokoro et al. |
| 6,463,361 B1 | 10/2002 | Wang et al. |
| 6,466,844 B1 | 10/2002 | Ikeda et al. |
| 6,468,265 B1 | 10/2002 | Evans et al. |
| 6,470,235 B2 | 10/2002 | Kasuga et al. |
| 6,474,434 B1 | 11/2002 | Bech |
| 6,480,762 B1 | 11/2002 | Uchikubo et al. |
| 6,491,701 B2 | 12/2002 | Tierney et al. |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury, Jr. et al. |
| 6,523,629 B1 | 2/2003 | Buttz et al. |
| 6,526,332 B2 | 2/2003 | Sakamoto et al. |
| 6,529,620 B2 | 3/2003 | Thompson |
| 6,529,765 B1 | 3/2003 | Franck et al. |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu et al. |
| 6,543,899 B2 | 4/2003 | Covannon et al. |
| 6,549,215 B2 | 4/2003 | Jouppi |
| 6,563,533 B1 | 5/2003 | Colby |
| 6,567,038 B1 | 5/2003 | Granot et al. |
| 6,580,246 B2 | 6/2003 | Jacobs |
| 6,581,798 B2 | 6/2003 | Liff et al. |
| 6,584,376 B1 | 6/2003 | Van Kommer |
| 6,587,750 B2 | 7/2003 | Gerbi et al. |
| 6,590,604 B1 | 7/2003 | Tucker et al. |
| 6,594,269 B1 | 7/2003 | Polcyn |
| 6,594,552 B1 | 7/2003 | Nowlin et al. |
| 6,597,392 B1 | 7/2003 | Jenkins et al. |
| 6,602,469 B1 | 8/2003 | Maus et al. |
| 6,604,019 B2 | 8/2003 | Ahlin et al. |
| 6,604,021 B2 | 8/2003 | Imai et al. |
| 6,611,120 B2 | 8/2003 | Song et al. |
| 6,643,496 B1 | 11/2003 | Shimoyama et al. |
| 6,646,677 B2 | 11/2003 | Noro et al. |
| 6,650,748 B1 | 11/2003 | Edwards et al. |
| 6,666,374 B1 | 12/2003 | Green et al. |
| 6,667,592 B2 | 12/2003 | Jacobs et al. |
| 6,674,259 B1 | 1/2004 | Norman et al. |
| 6,684,129 B2 | 1/2004 | Salisbury, Jr. et al. |
| 6,691,000 B2 | 2/2004 | Nagai et al. |
| 6,693,585 B1 | 2/2004 | MacLeod |
| 6,710,797 B1 | 3/2004 | McNelley et al. |
| 6,724,823 B2 | 4/2004 | Rovati et al. |
| 6,728,599 B2 | 4/2004 | Wang et al. |
| 6,763,282 B2 | 7/2004 | Glenn et al. |
| 6,763,284 B2 | 7/2004 | Watanabe et al. |
| 6,764,373 B1 | 7/2004 | Osawa et al. |
| 6,769,771 B2 | 8/2004 | Trumbull |
| 6,781,606 B2 | 8/2004 | Jouppi |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,816,192 B1 | 11/2004 | Nishikawa |
| 6,816,754 B2 | 11/2004 | Mukai et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,893,267 B1 | 5/2005 | Yueh |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe et al. |
| 6,957,712 B2 | 10/2005 | Song et al. |
| 6,958,706 B2 | 10/2005 | Chaco et al. |
| 6,965,394 B2 | 11/2005 | Gutta et al. |
| 6,990,112 B1 | 1/2006 | Brent et al. |
| 6,995,664 B1 | 2/2006 | Darling |
| 7,007,235 B1 | 2/2006 | Hussein et al. |
| 7,011,538 B2 | 3/2006 | Chang |
| 7,015,934 B2 | 3/2006 | Toyama et al. |
| RE39,080 E | 4/2006 | Johnston |
| 7,030,757 B2 | 4/2006 | Matsuhira et al. |
| 7,053,578 B2 | 5/2006 | Diehl et al. |
| 7,055,210 B2 | 6/2006 | Keppler et al. |
| 7,058,689 B2 | 6/2006 | Parker et al. |
| 7,092,001 B2 | 8/2006 | Schulz |

(56) References Cited

U.S. PATENT DOCUMENTS

| | | |
|---|---|---|
| 7,096,090 B1 | 8/2006 | Zweig |
| 7,115,102 B2 | 10/2006 | Abbruscato |
| 7,117,067 B2 | 10/2006 | McLurkin et al. |
| 7,123,285 B2 | 10/2006 | Smith et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 | 11/2006 | Wang et al. |
| 7,151,982 B2 | 12/2006 | Liff et al. |
| 7,154,526 B2 | 12/2006 | Foote et al. |
| 7,155,306 B2 | 12/2006 | Haitin et al. |
| 7,156,809 B2 | 1/2007 | Quy |
| 7,158,859 B2 | 1/2007 | Wang et al. |
| 7,158,860 B2 | 1/2007 | Wang et al. |
| 7,158,861 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |
| 7,164,970 B2 | 1/2007 | Wang et al. |
| 7,167,448 B2 | 1/2007 | Wookey et al. |
| 7,171,286 B2 | 1/2007 | Wang et al. |
| 7,174,238 B1 | 2/2007 | Zweig |
| 7,181,455 B2 | 2/2007 | Wookey et al. |
| 7,184,559 B2 | 2/2007 | Jouppi |
| 7,188,000 B2 | 3/2007 | Chiappetta et al. |
| 7,199,790 B2 | 4/2007 | Rosenberg et al. |
| 7,202,851 B2 | 4/2007 | Cunningham et al. |
| 7,206,627 B2 | 4/2007 | Abovitz et al. |
| 7,215,786 B2 | 5/2007 | Nakadai et al. |
| 7,219,364 B2 | 5/2007 | Bolle et al. |
| 7,222,000 B2 | 5/2007 | Wang et al. |
| 7,227,334 B2 | 6/2007 | Yang et al. |
| 7,256,708 B2 | 8/2007 | Rosenfeld et al. |
| 7,262,573 B2 | 8/2007 | Wang et al. |
| 7,283,153 B2 | 10/2007 | Provost et al. |
| 7,289,883 B2 | 10/2007 | Wang et al. |
| 7,292,257 B2 | 11/2007 | Kang et al. |
| 7,292,912 B2 | 11/2007 | Wang et al. |
| 7,305,114 B2 | 12/2007 | Wolff et al. |
| 7,317,685 B1 | 1/2008 | Flott et al. |
| 7,321,807 B2 | 1/2008 | Laski |
| 7,332,890 B2 | 2/2008 | Cohen et al. |
| 7,333,642 B2 | 2/2008 | Green |
| 7,346,429 B2 | 3/2008 | Goldenberg et al. |
| 7,352,153 B2 | 4/2008 | Yan |
| 7,363,121 B1 | 4/2008 | Chen et al. |
| 7,382,399 B1 | 6/2008 | McCall et al. |
| 7,386,730 B2 | 6/2008 | Uchikubo |
| 7,391,432 B2 | 6/2008 | Terada |
| 7,400,578 B2 | 7/2008 | Guthrie et al. |
| 7,404,140 B2 | 7/2008 | O'Rourke |
| 7,421,470 B2 | 9/2008 | Ludwig et al. |
| 7,430,209 B2 | 9/2008 | Porter |
| 7,432,949 B2 | 10/2008 | Remy et al. |
| 7,433,921 B2 | 10/2008 | Ludwig et al. |
| 7,441,953 B2 | 10/2008 | Banks |
| 7,467,211 B1 | 12/2008 | Herman et al. |
| 7,483,867 B2 | 1/2009 | Ansari et al. |
| 7,492,731 B2 | 2/2009 | Hagendorf |
| 7,510,428 B2 | 3/2009 | Obata et al. |
| 7,523,069 B1 | 4/2009 | Friedl et al. |
| 7,525,281 B2 | 4/2009 | Koyanagi et al. |
| 7,535,486 B2 | 5/2009 | Motomura et al. |
| 7,557,758 B2 | 7/2009 | Rofougaran |
| 7,587,260 B2 | 9/2009 | Bruemmer et al. |
| 7,587,512 B2 | 9/2009 | Ta et al. |
| 7,590,060 B2 | 9/2009 | Miceli |
| 7,593,030 B2 | 9/2009 | Wang et al. |
| 7,599,290 B2 | 10/2009 | Dos Remedios et al. |
| 7,624,166 B2 | 11/2009 | Foote et al. |
| 7,630,314 B2 | 12/2009 | Dos Remedios et al. |
| 7,631,833 B1 | 12/2009 | Ghaleb et al. |
| 7,643,051 B2 | 1/2010 | Sandberg et al. |
| 7,647,320 B2 | 1/2010 | Mok et al. |
| 7,657,560 B1 | 2/2010 | DiRienzo |
| 7,680,038 B1 | 3/2010 | Gourlay |
| 7,693,757 B2 | 4/2010 | Zimmerman |
| 7,698,432 B2 | 4/2010 | Short et al. |
| 7,703,113 B2 | 4/2010 | Dawson |
| 7,719,229 B2 | 5/2010 | Kaneko et al. |
| 7,737,993 B2 | 6/2010 | Kaasila et al. |
| 7,739,383 B1 | 6/2010 | Short et al. |
| 7,756,614 B2 | 7/2010 | Jouppi |
| 7,761,185 B2 | 7/2010 | Wang et al. |
| 7,769,492 B2 | 8/2010 | Wang et al. |
| 7,769,705 B1 | 8/2010 | Luechtefeld |
| 7,774,158 B2 | 8/2010 | Domingues Goncalves et al. |
| 7,797,168 B2 | 9/2010 | Kusumoto et al. |
| 7,813,836 B2 | 10/2010 | Wang et al. |
| 7,831,575 B2 | 11/2010 | Trossell et al. |
| 7,835,775 B2 | 11/2010 | Sawayama et al. |
| 7,860,680 B2 | 12/2010 | Arms et al. |
| 7,861,366 B2 | 1/2011 | Hahm et al. |
| 7,885,822 B2 | 2/2011 | Akers et al. |
| 7,890,382 B2 | 2/2011 | Robb et al. |
| 7,912,583 B2 | 3/2011 | Gutmann et al. |
| RE42,288 E | 4/2011 | Degioanni |
| 7,924,323 B2 | 4/2011 | Walker et al. |
| 7,949,616 B2 | 5/2011 | Levy et al. |
| 7,956,894 B2 | 6/2011 | Akers et al. |
| 7,957,837 B2 | 6/2011 | Ziegler et al. |
| 7,982,763 B2 | 7/2011 | King |
| 7,982,769 B2 | 7/2011 | Jenkins et al. |
| 7,987,069 B2 | 7/2011 | Rodgers et al. |
| 7,995,652 B2 | 8/2011 | Washington |
| 7,996,264 B2 | 8/2011 | Kusumoto et al. |
| 8,072,481 B1 | 12/2011 | McNelley et al. |
| 8,077,963 B2 | 12/2011 | Wang et al. |
| 8,116,910 B2 | 2/2012 | Walters et al. |
| 8,126,960 B2 | 2/2012 | Obradovich et al. |
| 8,170,241 B2 | 5/2012 | Roe et al. |
| 8,179,418 B2 | 5/2012 | Wright et al. |
| 8,180,486 B2 | 5/2012 | Saito et al. |
| 8,209,051 B2 | 6/2012 | Wang et al. |
| 8,212,533 B2 | 7/2012 | Ota |
| 8,265,793 B2 | 9/2012 | Cross et al. |
| 8,287,522 B2 | 10/2012 | Moses et al. |
| 8,292,807 B2 | 10/2012 | Perkins et al. |
| 8,320,534 B2 | 11/2012 | Kim et al. |
| 8,340,654 B2 | 12/2012 | Bratton et al. |
| 8,340,819 B2 | 12/2012 | Mangaser et al. |
| 8,348,675 B2 | 1/2013 | Dohrmann |
| 8,374,171 B2 | 2/2013 | Cho et al. |
| 8,384,755 B2 | 2/2013 | Wang et al. |
| 8,400,491 B1 | 3/2013 | Panpaliya et al. |
| 8,401,275 B2 | 3/2013 | Wang et al. |
| 8,423,284 B2 | 4/2013 | O'Shea |
| 8,451,731 B1 | 5/2013 | Lee et al. |
| 8,463,435 B2 | 6/2013 | Herzog et al. |
| 8,489,641 B1 | 7/2013 | Seefeldt et al. |
| 8,503,340 B1 | 8/2013 | Xu |
| 8,515,577 B2 | 8/2013 | Wang et al. |
| 8,527,094 B2 | 9/2013 | Kumar et al. |
| 8,531,502 B2 | 9/2013 | Cheng et al. |
| 8,532,860 B2 | 9/2013 | Daly |
| 8,588,976 B2 | 11/2013 | Mangaser et al. |
| 8,610,786 B2 | 12/2013 | Ortiz |
| 8,612,051 B2 | 12/2013 | Norman et al. |
| 8,639,797 B1 | 1/2014 | Pan et al. |
| 8,670,017 B2 | 3/2014 | Stuart et al. |
| 8,718,837 B2 | 5/2014 | Wang et al. |
| 8,726,454 B2 | 5/2014 | Gilbert, Jr. et al. |
| 8,750,906 B2 | 6/2014 | Winkler et al. |
| 8,776,043 B1 | 7/2014 | Thimsen et al. |
| 8,780,165 B2 | 7/2014 | Wang et al. |
| 8,836,751 B2 | 9/2014 | Ballantyne et al. |
| 8,849,679 B2 | 9/2014 | Wang et al. |
| 8,849,680 B2 | 9/2014 | Wright et al. |
| 8,861,750 B2 | 10/2014 | Roe et al. |
| 8,897,920 B2 | 11/2014 | Wang et al. |
| 8,902,278 B2 | 12/2014 | Pinter et al. |

(56) References Cited

U.S. PATENT DOCUMENTS

| | | |
|---|---|---|
| 8,983,174 B2 | 3/2015 | Wang et al. |
| 8,996,165 B2 | 3/2015 | Wang et al. |
| 9,098,611 B2 | 8/2015 | Pinter et al. |
| 9,147,284 B2 | 9/2015 | Keene et al. |
| 9,160,783 B2 | 10/2015 | Pinter |
| 9,198,728 B2 | 12/2015 | Wang et al. |
| 9,251,313 B2 | 2/2016 | Ross et al. |
| 9,264,664 B2 | 2/2016 | Pinter et al. |
| 9,361,021 B2 | 6/2016 | Jordan et al. |
| 9,374,363 B1 * | 6/2016 | Paczkowski ............ G06F 21/32 |
| 2001/0002448 A1 | 5/2001 | Wilson et al. |
| 2001/0010053 A1 | 7/2001 | Ben-shachar et al. |
| 2001/0010541 A1 | 8/2001 | Fernandez et al. |
| 2001/0020200 A1 | 9/2001 | Das et al. |
| 2001/0034475 A1 | 10/2001 | Flach et al. |
| 2001/0034544 A1 | 10/2001 | Mo |
| 2001/0037163 A1 | 11/2001 | Allard |
| 2001/0048464 A1 | 12/2001 | Barnett |
| 2001/0051881 A1 | 12/2001 | Filler |
| 2001/0054071 A1 | 12/2001 | Loeb |
| 2001/0055373 A1 | 12/2001 | Yamashita |
| 2002/0010596 A1 | 1/2002 | Matory |
| 2002/0015296 A1 | 2/2002 | Howell et al. |
| 2002/0027597 A1 | 3/2002 | Sachau |
| 2002/0027652 A1 | 3/2002 | Paromtchik et al. |
| 2002/0033880 A1 | 3/2002 | Sul et al. |
| 2002/0038168 A1 | 3/2002 | Kasuga et al. |
| 2002/0044201 A1 | 4/2002 | Alexander et al. |
| 2002/0049517 A1 | 4/2002 | Ruffner |
| 2002/0055917 A1 | 5/2002 | Muraca |
| 2002/0057279 A1 | 5/2002 | Jouppi |
| 2002/0058929 A1 | 5/2002 | Green |
| 2002/0059587 A1 | 5/2002 | Cofano et al. |
| 2002/0063726 A1 | 5/2002 | Jouppi |
| 2002/0073429 A1 | 6/2002 | Beane et al. |
| 2002/0082498 A1 | 6/2002 | Wendt et al. |
| 2002/0085030 A1 | 7/2002 | Ghani |
| 2002/0095238 A1 | 7/2002 | Ahlin et al. |
| 2002/0095239 A1 | 7/2002 | Wallach et al. |
| 2002/0098879 A1 | 7/2002 | Rheey |
| 2002/0104094 A1 | 8/2002 | Alexander et al. |
| 2002/0106998 A1 | 8/2002 | Presley et al. |
| 2002/0109770 A1 | 8/2002 | Terada |
| 2002/0109775 A1 | 8/2002 | White et al. |
| 2002/0111988 A1 | 8/2002 | Sato |
| 2002/0120362 A1 | 8/2002 | Lathan et al. |
| 2002/0123941 A1 | 9/2002 | Donahue et al. |
| 2002/0128985 A1 | 9/2002 | Greenwald |
| 2002/0130950 A1 | 9/2002 | James et al. |
| 2002/0133062 A1 | 9/2002 | Arling et al. |
| 2002/0141595 A1 | 10/2002 | Jouppi |
| 2002/0143923 A1 | 10/2002 | Alexander |
| 2002/0177925 A1 | 11/2002 | Onishi et al. |
| 2002/0183598 A1 | 12/2002 | Teraura et al. |
| 2002/0183894 A1 | 12/2002 | Wang et al. |
| 2002/0184674 A1 | 12/2002 | Xi et al. |
| 2002/0186243 A1 | 12/2002 | Ellis et al. |
| 2002/0193908 A1 | 12/2002 | Parker et al. |
| 2003/0021107 A1 | 1/2003 | Howell et al. |
| 2003/0030397 A1 | 2/2003 | Simmons |
| 2003/0048481 A1 | 3/2003 | Kobayashi et al. |
| 2003/0050733 A1 | 3/2003 | Wang et al. |
| 2003/0050734 A1 | 3/2003 | Lapham |
| 2003/0060808 A1 | 3/2003 | Wilk |
| 2003/0063600 A1 | 4/2003 | Noma et al. |
| 2003/0069752 A1 | 4/2003 | Ledain et al. |
| 2003/0069828 A1 | 4/2003 | Blazey et al. |
| 2003/0080901 A1 | 5/2003 | Piotrowski |
| 2003/0100892 A1 | 5/2003 | Morley et al. |
| 2003/0104806 A1 | 6/2003 | Ruef et al. |
| 2003/0112823 A1 | 6/2003 | Collins et al. |
| 2003/0114962 A1 | 6/2003 | Niemeyer |
| 2003/0120714 A1 | 6/2003 | Wolff et al. |
| 2003/0126361 A1 | 7/2003 | Slater et al. |
| 2003/0135097 A1 | 7/2003 | Wiederhold et al. |
| 2003/0135203 A1 | 7/2003 | Wang et al. |
| 2003/0144579 A1 | 7/2003 | Buss |
| 2003/0144649 A1 | 7/2003 | Ghodoussi et al. |
| 2003/0151658 A1 | 8/2003 | Smith |
| 2003/0152145 A1 | 8/2003 | Kawakita |
| 2003/0171710 A1 | 9/2003 | Bassuk et al. |
| 2003/0174285 A1 | 9/2003 | Trumbull |
| 2003/0180697 A1 | 9/2003 | Kim et al. |
| 2003/0195662 A1 | 10/2003 | Wang et al. |
| 2003/0199000 A1 | 10/2003 | Valkirs et al. |
| 2003/0206242 A1 | 11/2003 | Choi |
| 2003/0212472 A1 | 11/2003 | Mckee |
| 2003/0216833 A1 | 11/2003 | Mukai et al. |
| 2003/0216834 A1 | 11/2003 | Allard |
| 2003/0220541 A1 | 11/2003 | Salisbury et al. |
| 2003/0220715 A1 | 11/2003 | Kneifel et al. |
| 2003/0231244 A1 | 12/2003 | Bonilla et al. |
| 2003/0232649 A1 | 12/2003 | Gizis et al. |
| 2003/0236590 A1 | 12/2003 | Park et al. |
| 2004/0001197 A1 | 1/2004 | Ko et al. |
| 2004/0001676 A1 | 1/2004 | Colgan et al. |
| 2004/0008138 A1 | 1/2004 | Hockley et al. |
| 2004/0010344 A1 | 1/2004 | Hiratsuka et al. |
| 2004/0012362 A1 | 1/2004 | Tsurumi |
| 2004/0013295 A1 | 1/2004 | Sabe et al. |
| 2004/0015265 A1 | 1/2004 | Asano et al. |
| 2004/0017475 A1 | 1/2004 | Akers et al. |
| 2004/0019406 A1 | 1/2004 | Wang et al. |
| 2004/0024490 A1 | 2/2004 | Mclurkin et al. |
| 2004/0041904 A1 | 3/2004 | Lapalme et al. |
| 2004/0048633 A1 | 3/2004 | Sato et al. |
| 2004/0065073 A1 | 4/2004 | Nash |
| 2004/0068657 A1 | 4/2004 | Alexander et al. |
| 2004/0078219 A1 | 4/2004 | Kaylor et al. |
| 2004/0080610 A1 | 4/2004 | James et al. |
| 2004/0088077 A1 | 5/2004 | Jouppi et al. |
| 2004/0088078 A1 | 5/2004 | Jouppi et al. |
| 2004/0093409 A1 | 5/2004 | Thompson et al. |
| 2004/0095516 A1 | 5/2004 | Rohlicek |
| 2004/0098167 A1 | 5/2004 | Yi et al. |
| 2004/0102167 A1 | 5/2004 | Shim et al. |
| 2004/0107254 A1 | 6/2004 | Ludwig et al. |
| 2004/0107255 A1 | 6/2004 | Ludwig et al. |
| 2004/0117065 A1 | 6/2004 | Wang et al. |
| 2004/0117067 A1 | 6/2004 | Jouppi |
| 2004/0123158 A1 | 6/2004 | Roskind |
| 2004/0135879 A1 | 7/2004 | Stacy et al. |
| 2004/0138547 A1 | 7/2004 | Wang et al. |
| 2004/0140404 A1 | 7/2004 | Ohta et al. |
| 2004/0143421 A1 | 7/2004 | Wang et al. |
| 2004/0148638 A1 | 7/2004 | Weisman et al. |
| 2004/0150725 A1 | 8/2004 | Taguchi |
| 2004/0153211 A1 | 8/2004 | Kamoto et al. |
| 2004/0157612 A1 | 8/2004 | Kim |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0168148 A1 | 8/2004 | Goncalves et al. |
| 2004/0170300 A1 | 9/2004 | Jouppi |
| 2004/0172301 A1 | 9/2004 | Mihai et al. |
| 2004/0172306 A1 | 9/2004 | Wohl et al. |
| 2004/0174129 A1 | 9/2004 | Wang et al. |
| 2004/0175684 A1 | 9/2004 | Kaasa et al. |
| 2004/0179714 A1 | 9/2004 | Jouppi |
| 2004/0186623 A1 | 9/2004 | Dooley et al. |
| 2004/0189700 A1 | 9/2004 | Mandavilli et al. |
| 2004/0201602 A1 | 10/2004 | Mody et al. |
| 2004/0202281 A1 | 10/2004 | Colbeth et al. |
| 2004/0205664 A1 | 10/2004 | Prendergast |
| 2004/0215490 A1 | 10/2004 | Duchon et al. |
| 2004/0218099 A1 | 11/2004 | Washington |
| 2004/0222638 A1 | 11/2004 | Bednyak |
| 2004/0224676 A1 | 11/2004 | Iseki |
| 2004/0230340 A1 | 11/2004 | Fukuchi et al. |
| 2004/0240981 A1 | 12/2004 | Dothan et al. |
| 2004/0241981 A1 | 12/2004 | Doris et al. |
| 2004/0243712 A1 | 12/2004 | Sakai et al. |
| 2004/0260790 A1 | 12/2004 | Balloni et al. |
| 2005/0003330 A1 | 1/2005 | Asgarinejad et al. |

(56) References Cited

U.S. PATENT DOCUMENTS

| | | |
|---|---|---|
| 2005/0004708 A1 | 1/2005 | Goldenberg et al. |
| 2005/0007445 A1 | 1/2005 | Foote et al. |
| 2005/0013149 A1 | 1/2005 | Trossell |
| 2005/0021182 A1 | 1/2005 | Wang et al. |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick |
| 2005/0049898 A1 | 3/2005 | Hirakawa |
| 2005/0052527 A1 | 3/2005 | Remy et al. |
| 2005/0060211 A1 | 3/2005 | Xiao et al. |
| 2005/0065435 A1 | 3/2005 | Rauch et al. |
| 2005/0065438 A1 | 3/2005 | Miller |
| 2005/0065659 A1 | 3/2005 | Tanaka et al. |
| 2005/0065813 A1 | 3/2005 | Mishelevich et al. |
| 2005/0071046 A1 | 3/2005 | Miyazaki et al. |
| 2005/0073575 A1 | 4/2005 | Thacher et al. |
| 2005/0075544 A1 | 4/2005 | Shapiro et al. |
| 2005/0078816 A1 | 4/2005 | Sekiguchi et al. |
| 2005/0083011 A1 | 4/2005 | Yang et al. |
| 2005/0099493 A1 | 5/2005 | Chew |
| 2005/0104964 A1 | 5/2005 | Bovyrin et al. |
| 2005/0110867 A1 | 5/2005 | Schulz |
| 2005/0122390 A1 | 6/2005 | Wang et al. |
| 2005/0125083 A1 | 6/2005 | Kiko |
| 2005/0125098 A1 | 6/2005 | Wang et al. |
| 2005/0149364 A1 | 7/2005 | Ombrellaro |
| 2005/0152447 A1 | 7/2005 | Jouppi et al. |
| 2005/0152565 A1 | 7/2005 | Jouppi et al. |
| 2005/0154265 A1 | 7/2005 | Miro et al. |
| 2005/0168568 A1 | 8/2005 | Jouppi |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1 | 10/2005 | Smith et al. |
| 2005/0225634 A1 | 10/2005 | Brunetti et al. |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | Mcgee et al. |
| 2005/0264648 A1 | 12/2005 | Ivashin et al. |
| 2005/0264649 A1 | 12/2005 | Chang et al. |
| 2005/0267826 A1 | 12/2005 | Levy et al. |
| 2005/0283414 A1 | 12/2005 | Fernandes et al. |
| 2005/0286759 A1 | 12/2005 | Zitnick et al. |
| 2006/0007943 A1 | 1/2006 | Fellman |
| 2006/0010028 A1 | 1/2006 | Sorensen |
| 2006/0013263 A1 | 1/2006 | Fellman |
| 2006/0013469 A1 | 1/2006 | Wang et al. |
| 2006/0013488 A1 | 1/2006 | Inoue |
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047365 A1 | 3/2006 | Ghodoussi et al. |
| 2006/0048286 A1 | 3/2006 | Donato |
| 2006/0052676 A1 | 3/2006 | Wang et al. |
| 2006/0052684 A1 | 3/2006 | Takahashi et al. |
| 2006/0056655 A1 | 3/2006 | Wen et al. |
| 2006/0056837 A1 | 3/2006 | Vapaakoski |
| 2006/0064212 A1 | 3/2006 | Thorne |
| 2006/0066609 A1 | 3/2006 | Iodice et al. |
| 2006/0071797 A1 | 4/2006 | Rosenfeld et al. |
| 2006/0074525 A1 | 4/2006 | Close et al. |
| 2006/0074719 A1 | 4/2006 | Horner |
| 2006/0082642 A1 | 4/2006 | Wang et al. |
| 2006/0087746 A1 | 4/2006 | Lipow |
| 2006/0089765 A1 | 4/2006 | Pack et al. |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0119701 A1 | 6/2006 | King |
| 2006/0122482 A1 | 6/2006 | Mariotti et al. |
| 2006/0125356 A1 | 6/2006 | Meek et al. |
| 2006/0142983 A1 | 6/2006 | Sorensen et al. |
| 2006/0149418 A1 | 7/2006 | Anvari |
| 2006/0161136 A1 | 7/2006 | Anderson et al. |
| 2006/0161303 A1 | 7/2006 | Wang et al. |
| 2006/0164546 A1 | 7/2006 | Adachi |
| 2006/0171515 A1 | 8/2006 | Hintermeister et al. |
| 2006/0173708 A1 | 8/2006 | Vining et al. |
| 2006/0173712 A1 | 8/2006 | Joubert |
| 2006/0178559 A1 | 8/2006 | Kumar et al. |
| 2006/0178776 A1 | 8/2006 | Feingold et al. |
| 2006/0178777 A1 | 8/2006 | Park et al. |
| 2006/0189393 A1 | 8/2006 | Edery |
| 2006/0195569 A1 | 8/2006 | Barker |
| 2006/0224781 A1 | 10/2006 | Tsao et al. |
| 2006/0238379 A1 | 10/2006 | Kimchi et al. |
| 2006/0247045 A1 | 11/2006 | Jeong et al. |
| 2006/0259193 A1 | 11/2006 | Wang et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0016328 A1 | 1/2007 | Ziegler et al. |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0061041 A1 | 3/2007 | Zweig |
| 2007/0064092 A1 | 3/2007 | Sandbeg et al. |
| 2007/0067734 A1 | 3/2007 | Cunningham et al. |
| 2007/0078566 A1 | 4/2007 | Wang et al. |
| 2007/0093279 A1 | 4/2007 | Janik |
| 2007/0112700 A1 | 5/2007 | Den haan et al. |
| 2007/0116152 A1 | 5/2007 | Thesling |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0170886 A1 | 7/2007 | Plishner |
| 2007/0176060 A1 | 8/2007 | White et al. |
| 2007/0182811 A1 | 8/2007 | Rockefeller et al. |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0226949 A1 | 10/2007 | Hahm et al. |
| 2007/0250212 A1 | 10/2007 | Halloran et al. |
| 2007/0255706 A1 | 11/2007 | Iketani et al. |
| 2007/0262884 A1 | 11/2007 | Goncalves et al. |
| 2007/0273751 A1 | 11/2007 | Sachau |
| 2007/0290040 A1 | 12/2007 | Wurman et al. |
| 2007/0291109 A1 | 12/2007 | Wang et al. |
| 2007/0291128 A1 | 12/2007 | Wang et al. |
| 2008/0009969 A1 | 1/2008 | Bruemmer et al. |
| 2008/0011904 A1 | 1/2008 | Cepollina et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0051985 A1 | 2/2008 | D'andrea et al. |
| 2008/0065268 A1 | 3/2008 | Wang et al. |
| 2008/0082211 A1 | 4/2008 | Wang et al. |
| 2008/0086241 A1 | 4/2008 | Phillips et al. |
| 2008/0091340 A1 | 4/2008 | Milstein et al. |
| 2008/0126132 A1 | 5/2008 | Warner et al. |
| 2008/0133052 A1 | 6/2008 | Jones et al. |
| 2008/0161969 A1 | 7/2008 | Lee et al. |
| 2008/0174570 A1 | 7/2008 | Jobs et al. |
| 2008/0201016 A1 | 8/2008 | Finlay |

(56) References Cited

U.S. PATENT DOCUMENTS

| | | |
|---|---|---|
| 2008/0201017 A1 | 8/2008 | Wang et al. |
| 2008/0215987 A1 | 9/2008 | Alexander et al. |
| 2008/0229531 A1 | 9/2008 | Takida |
| 2008/0232763 A1 | 9/2008 | Brady |
| 2008/0255703 A1 | 10/2008 | Wang et al. |
| 2008/0263451 A1 | 10/2008 | Portele et al. |
| 2008/0263628 A1 | 10/2008 | Norman et al. |
| 2008/0267069 A1 | 10/2008 | Thielman et al. |
| 2008/0269949 A1 | 10/2008 | Norman et al. |
| 2008/0281467 A1 | 11/2008 | Pinter |
| 2008/0285886 A1 | 11/2008 | Allen |
| 2008/0306375 A1 | 12/2008 | Sayler et al. |
| 2009/0021572 A1 | 1/2009 | Garudadri et al. |
| 2009/0030552 A1 | 1/2009 | Nakadai et al. |
| 2009/0044334 A1 | 2/2009 | Parsell et al. |
| 2009/0049640 A1 | 2/2009 | Lee et al. |
| 2009/0055023 A1 | 2/2009 | Walters et al. |
| 2009/0070135 A1 | 3/2009 | Parida et al. |
| 2009/0086013 A1 | 4/2009 | Thapa |
| 2009/0102919 A1 | 4/2009 | Zamierowski et al. |
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0144425 A1 | 6/2009 | Marr et al. |
| 2009/0164255 A1 | 6/2009 | Menschik et al. |
| 2009/0164657 A1 | 6/2009 | Li et al. |
| 2009/0171170 A1 | 7/2009 | Li et al. |
| 2009/0173846 A1 | 7/2009 | Katz |
| 2009/0177323 A1 | 7/2009 | Ziegler et al. |
| 2009/0177641 A1 | 7/2009 | Raghavan |
| 2009/0234499 A1 | 9/2009 | Nielsen et al. |
| 2009/0237317 A1 | 9/2009 | Rofougaran |
| 2009/0240371 A1 | 9/2009 | Wang et al. |
| 2009/0248041 A1 | 10/2009 | Williams et al. |
| 2009/0248200 A1 | 10/2009 | Root |
| 2009/0259339 A1 | 10/2009 | Wright et al. |
| 2010/0010672 A1 | 1/2010 | Wang et al. |
| 2010/0010673 A1 | 1/2010 | Wang et al. |
| 2010/0017046 A1 | 1/2010 | Cheung et al. |
| 2010/0019715 A1 | 1/2010 | Roe et al. |
| 2010/0026239 A1 | 2/2010 | Li et al. |
| 2010/0030578 A1 | 2/2010 | Siddique et al. |
| 2010/0051596 A1 | 3/2010 | Diedrick et al. |
| 2010/0063848 A1 | 3/2010 | Kremer et al. |
| 2010/0066804 A1 | 3/2010 | Shoemake et al. |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0085874 A1 | 4/2010 | Noy et al. |
| 2010/0088232 A1 | 4/2010 | Gale |
| 2010/0115418 A1 | 5/2010 | Wang et al. |
| 2010/0116566 A1 | 5/2010 | Ohm et al. |
| 2010/0121577 A1 | 5/2010 | Zhang et al. |
| 2010/0131103 A1 | 5/2010 | Herzog et al. |
| 2010/0145479 A1 | 6/2010 | Griffiths |
| 2010/0157825 A1 | 6/2010 | Anderlind et al. |
| 2010/0171826 A1 | 7/2010 | Hamilton et al. |
| 2010/0191375 A1 | 7/2010 | Wright et al. |
| 2010/0198608 A1* | 8/2010 | Kaboff ............ G16H 40/67 715/741 |
| 2010/0228249 A1 | 9/2010 | Mohr et al. |
| 2010/0268383 A1 | 10/2010 | Wang et al. |
| 2010/0278086 A1 | 11/2010 | Pochiraju et al. |
| 2010/0286905 A1 | 11/2010 | Goncalves et al. |
| 2010/0301679 A1 | 12/2010 | Murray et al. |
| 2010/0323783 A1 | 12/2010 | Nonaka et al. |
| 2011/0022705 A1 | 1/2011 | Yellamraju et al. |
| 2011/0050841 A1 | 3/2011 | Wang et al. |
| 2011/0071675 A1 | 3/2011 | Wells et al. |
| 2011/0071702 A1 | 3/2011 | Wang et al. |
| 2011/0072114 A1 | 3/2011 | Hoffert et al. |
| 2011/0118748 A1 | 5/2011 | Itkowitz |
| 2011/0153198 A1 | 6/2011 | Kokkas et al. |
| 2011/0169832 A1 | 7/2011 | Brown et al. |
| 2011/0172822 A1 | 7/2011 | Ziegler et al. |
| 2011/0187875 A1 | 8/2011 | Sanchez et al. |
| 2011/0190930 A1 | 8/2011 | Hanrahan et al. |
| 2011/0193949 A1 | 8/2011 | Nambakam et al. |
| 2011/0195701 A1 | 8/2011 | Cook et al. |
| 2011/0213210 A1 | 9/2011 | Temby et al. |
| 2011/0218674 A1 | 9/2011 | Stuart et al. |
| 2011/0245973 A1 | 10/2011 | Wang et al. |
| 2011/0249079 A1 | 10/2011 | Santamaria et al. |
| 2011/0280551 A1 | 11/2011 | Sammon |
| 2011/0288417 A1 | 11/2011 | Pinter et al. |
| 2011/0292193 A1 | 12/2011 | Wang et al. |
| 2011/0301759 A1 | 12/2011 | Wang et al. |
| 2011/0306400 A1 | 12/2011 | Nguyen |
| 2012/0023506 A1 | 1/2012 | Maeckel et al. |
| 2012/0036484 A1 | 2/2012 | Zhang et al. |
| 2012/0059946 A1 | 3/2012 | Wang |
| 2012/0072023 A1 | 3/2012 | Ota |
| 2012/0072024 A1 | 3/2012 | Wang et al. |
| 2012/0092157 A1 | 4/2012 | Tran |
| 2012/0095352 A1 | 4/2012 | Tran |
| 2012/0095619 A1 | 4/2012 | Pack et al. |
| 2012/0113856 A1 | 5/2012 | Krishnaswamy |
| 2012/0182392 A1 | 7/2012 | Kearns et al. |
| 2012/0191246 A1 | 7/2012 | Roe et al. |
| 2012/0191464 A1 | 7/2012 | Stuart et al. |
| 2012/0203731 A1 | 8/2012 | Nelson et al. |
| 2012/0215380 A1 | 8/2012 | Fouillade et al. |
| 2012/0218374 A1 | 8/2012 | Matula et al. |
| 2012/0220372 A1 | 8/2012 | Cheung et al. |
| 2012/0242279 A1 | 9/2012 | Tso et al. |
| 2012/0291809 A1 | 11/2012 | Kuhe et al. |
| 2013/0035138 A1 | 2/2013 | Abbott |
| 2013/0158720 A1 | 6/2013 | Zywicki et al. |
| 2013/0250938 A1 | 9/2013 | Anandakumar et al. |
| 2013/0321257 A1 | 12/2013 | Moore et al. |
| 2014/0015914 A1 | 1/2014 | Delaunay |
| 2014/0032244 A1 | 1/2014 | Kolls et al. |
| 2014/0047022 A1 | 2/2014 | Chan et al. |
| 2014/0085543 A1 | 3/2014 | Hartley et al. |
| 2014/0135990 A1 | 5/2014 | Stuart et al. |
| 2014/0139616 A1 | 5/2014 | Pinter et al. |
| 2014/0155755 A1 | 6/2014 | Pinter et al. |
| 2014/0250191 A1 | 9/2014 | Altman et al. |
| 2015/0119652 A1 | 4/2015 | Hyde et al. |
| 2015/0298317 A1 | 10/2015 | Wang et al. |

FOREIGN PATENT DOCUMENTS

| | | |
|---|---|---|
| CN | 1404695 A | 3/2003 |
| CN | 1554193 A | 12/2004 |
| CN | 1554985 A | 12/2004 |
| CN | 1561923 A | 1/2005 |
| CN | 1743144 A | 3/2006 |
| CN | 101049017 A | 10/2007 |
| CN | 101106939 A | 1/2008 |
| CN | 101151614 A | 3/2008 |
| CN | 100407729 C | 7/2008 |
| CN | 101390098 A | 3/2009 |
| CN | 101507260 A | 8/2009 |
| CN | 101730894 A | 6/2010 |
| CN | 101866396 A | 10/2010 |
| CN | 101978365 A | 2/2011 |
| CN | 102203759 A | 9/2011 |
| CN | 101106939 B | 11/2011 |
| EP | 466492 A2 | 1/1992 |
| EP | 488673 A2 | 6/1992 |
| EP | 0981905 B1 | 1/2002 |
| EP | 1262142 A2 | 12/2002 |
| EP | 1304872 A1 | 4/2003 |
| EP | 1536660 A2 | 6/2005 |
| EP | 1573406 A2 | 9/2005 |
| EP | 1594660 A2 | 11/2005 |
| EP | 1763243 A2 | 3/2007 |
| EP | 1791464 A2 | 6/2007 |
| EP | 1800476 A2 | 6/2007 |
| EP | 1819108 A2 | 8/2007 |
| EP | 1856644 A2 | 11/2007 |
| EP | 1536660 A3 | 4/2008 |

(56) References Cited

FOREIGN PATENT DOCUMENTS

| | | | |
|---|---|---|---|
| EP | 1928310 A2 | 6/2008 | |
| EP | 1232610 B1 | 1/2009 | |
| EP | 2027716 A2 | 2/2009 | |
| EP | 2145274 A1 | 1/2010 | |
| EP | 2214111 A2 | 8/2010 | |
| EP | 2263158 A2 | 12/2010 | |
| EP | 2300930 A1 | 3/2011 | |
| EP | 2342651 A1 | 7/2011 | |
| EP | 2300930 B1 | 7/2015 | |
| GB | 2431261 A | 4/2007 | |
| GB | 2477837 A * | 8/2011 | ........... G06F 21/316 |
| JP | H07-194609 A | 8/1995 | |
| JP | H07-213753 A | 8/1995 | |
| JP | H07-248823 A | 9/1995 | |
| JP | H07-257422 A | 10/1995 | |
| JP | H08-84328 A | 3/1996 | |
| JP | H08-320727 A | 12/1996 | |
| JP | H09-267276 A | 10/1997 | |
| JP | H10-79097 A | 3/1998 | |
| JP | H10-288689 A | 10/1998 | |
| JP | H11-220706 A | 8/1999 | |
| JP | 2000-032319 A | 1/2000 | |
| JP | 2000-049800 A | 2/2000 | |
| JP | 2000-079587 A | 3/2000 | |
| JP | 2000-196876 A | 7/2000 | |
| JP | 2001-125641 A | 5/2001 | |
| JP | 2001-147718 A | 5/2001 | |
| JP | 2001-179663 A | 7/2001 | |
| JP | 2001-188124 A | 7/2001 | |
| JP | 2001-198865 A | 7/2001 | |
| JP | 2001-198868 A | 7/2001 | |
| JP | 2001-199356 A | 7/2001 | |
| JP | 2002-000574 A | 1/2002 | |
| JP | 2002-046088 A | 2/2002 | |
| JP | 2002-101333 A | 4/2002 | |
| JP | 2002-112970 A | 4/2002 | |
| JP | 2002-235423 A | 8/2002 | |
| JP | 2002-305743 A | 10/2002 | |
| JP | 2002-321180 A | 11/2002 | |
| JP | 2002-355779 A | 12/2002 | |
| JP | 2004-181229 A | 7/2004 | |
| JP | 2004-524824 T | 8/2004 | |
| JP | 2004-261941 A | 9/2004 | |
| JP | 2004-289379 A | 10/2004 | |
| JP | 2005-028066 A | 2/2005 | |
| JP | 2005-059170 A | 3/2005 | |
| JP | 2005-111083 A | 4/2005 | |
| JP | 2006-508806 A | 3/2006 | |
| JP | 2006-109094 A | 4/2006 | |
| JP | 2006-224294 A | 8/2006 | |
| JP | 2006-246438 A | 9/2006 | |
| JP | 2007-007040 A | 1/2007 | |
| JP | 2007-081646 A | 3/2007 | |
| JP | 2007-232208 A | 9/2007 | |
| JP | 2007-316966 A | 12/2007 | |
| JP | 2009-125133 A | 6/2009 | |
| JP | 2010-064154 A | 3/2010 | |
| JP | 2010-532109 A | 9/2010 | |
| JP | 2010-246954 A | 11/2010 | |
| KR | 10-2006-0037979 A | 5/2006 | |
| KR | 10-2009-0012542 A | 2/2009 | |
| KR | 10-2010-0019479 A | 2/2010 | |
| KR | 10-2010-0139037 A | 12/2010 | |
| WO | 93/06690 A1 | 4/1993 | |
| WO | 97/42761 A1 | 11/1997 | |
| WO | 1998/51078 A1 | 11/1998 | |
| WO | 99/67067 A1 | 12/1999 | |
| WO | 2000/025516 A1 | 5/2000 | |
| WO | 2000/033726 A1 | 6/2000 | |
| WO | 01/31861 A1 | 5/2001 | |
| WO | 2003/077745 A1 | 9/2003 | |
| WO | 2004/008738 A1 | 1/2004 | |
| WO | 2004/012018 A2 | 2/2004 | |
| WO | 2004/075456 A2 | 9/2004 | |
| WO | 2006/012797 A1 | 2/2006 | |
| WO | 2006/044847 A2 | 4/2006 | |
| WO | 2006/078611 A2 | 7/2006 | |
| WO | 2007/041038 A3 | 4/2007 | |
| WO | 2007/041295 A2 | 4/2007 | |
| WO | 2008/100272 A2 | 8/2008 | |
| WO | 2008/100272 A3 | 10/2008 | |
| WO | 2009/117274 A2 | 9/2009 | |
| WO | 2009/128997 A1 | 10/2009 | |
| WO | 2009/145958 A2 | 12/2009 | |
| WO | 2010/006205 A1 | 1/2010 | |
| WO | 2010/006211 A1 | 1/2010 | |
| WO | 2010/033666 A1 | 3/2010 | |
| WO | 2010/047881 A1 | 4/2010 | |
| WO | 2010/062798 A1 | 6/2010 | |
| WO | 2010/065257 A1 | 6/2010 | |
| WO | 2010/120407 A1 | 10/2010 | |
| WO | 2011/028589 A2 | 3/2011 | |
| WO | 2011/028589 A3 | 4/2011 | |
| WO | 2011/097130 A2 | 8/2011 | |
| WO | 2011/097132 A2 | 8/2011 | |
| WO | 2011/109336 A2 | 9/2011 | |
| WO | 2011/097132 A3 | 12/2011 | |
| WO | 2011/149902 A2 | 12/2011 | |
| WO | 2013/097264 A1 | 7/2013 | |

OTHER PUBLICATIONS

Jouppi et al., "BiReality: Mutually-Immersive Telepresence", Proceedings of the 12th Annual ACM International Conference on Multimedia, Oct. 10-16, 2004, pp. 860-867.

Jouppi et al., "First Steps Towards Mutually-Immersive Mobile Telepresence", Proceedings of the 2002 ACM Conference on Computer Supported Cooperative Work, Nov. 16-20, 2002, pp. 354-363.

Kanehiro et al., "Virtual Humanoid Robot Platform to Develop Controllers of Real Humanoid Robots without Porting", IEEE/RSJ International Conference on Intelligent Robots and Systems, vol. 2, 2001, pp. 1093-1099.

Kaplan et al., "An Internet Accessible Telepresence", Multimedia Systems Journal, vol. 5, 1996, 7 pages.

Keller et al., "Raven Interface Project", The National Aviary's Teleconferencing Carnegie Mellon University Robot, Interaction and Visual Interface Design, School of Design, Carnegie Mellon University, 2001, 8 pages.

Khatib et al., "Robots in Human Environments", Proceedings International Conference on Control, Automation, Robotics, and Vision ICRACV2000, 1999, 15 pages.

Knight et al., "Active Visual Alignment of a Mobile Stereo Camera Platform", IEEE International Conference on Robotics and Automation, vol. 4, Apr. 24-28, 2000, pp. 3203-3208.

Koenen, Rob, "MPEG-4: a Powerful Standard for Use in Web and Television Environments", (KPN Research), available online at <http://www.w3.org/Architecture/1998/06/Workshop/paper26>, Jul. 1, 1998, 4 pages.

Kurlowicz et al., "The Mini Mental State Examination (MMSE)", Try This: Best Practices in Nursing Care to Older Adults, A series from the Hartford Institute of Geriatric Nursing, Issue No. 3, Jan. 1999, 2 pages.

Kuzuoka et al., "Can the GestureCam Be a Surrogate?", Proceedings of the Fourth European Conference on Computer-Supported Cooperative Work, 1995, pp. 181-196.

Lane, Earl, "Automated Aides", Available online at <http://www.cs.cum.edu/nursebot/web/press/nd4380.htm>, Oct. 17, 2000, 4 pages.

Lee et al., "A Novel Method of Surgical Instruction: International Telementoring", World Journal of Urology, vol. 16, No. 6, Dec. 1998, pp. 367-370.

Leifer et al., "VIPRR: A Virtually In Person Rehabilitation Robot", Proceedings of 1997 International Conference on Rehabilitation Robotics, Apr. 14-15, 1997, 4 pages.

Lemaire, Edward, "Using Communication Technology to Enhance Rehabilitation Services: A Solution Oriented User Manual", Institute for Rehabilitation Research and Development, Terry Fox Mobile Clinic, The Rehabilitation Centre, Ottawa, Ontario, Canada, Version 2.0, available online at <http://www.irrd.ca/telehealth/distfile/distman_v2_1.pdf>, 1998-2001, 104 pages.

(56) References Cited

OTHER PUBLICATIONS

Library of Congress, "008—Fixed-Length Data Elements (NR)", MARC 21 Format for Classification Data, available online at <http://www.loc.gov/marc/classification/cd008.html>, Jan. 2000, pp. 1-14.

Lim et al., "Control to Realize Human-Like Walking of a Biped Humanoid Robot", IEEE International Conference on Systems, Man, and Cybernetics, 2000, vol. 5, 2000, pp. 3271-3276.

Linebarger et al., "Concurrency Control Mechanisms for Closely Coupled Collaboration in Multithreaded Virtual Environments", Department of Computer Science and Engineering, Lehigh University, vol. 13, 2004, 40 pages.

Long, William F., "Robot Navigation Technology", available online at <http://www.atp.nist.gov/eao/sp950-1/helpmate.htm>, Mar. 1999, 3 pages.

Luna, Nancy, "Robot a New Face on Geriatric Care", ocregister.com, Aug. 6, 2003, 3 pages.

Mack, Michael J., "Minimally Invasive and Robotic Surgery", The Journal of the American Medical Association, vol. 285, No. 5, 2001, pp. 568-572.

Mair, G. M., "Telepresence—The Technology and its Economic and Social Implications", Technology and Society, 1997. 'Technology and Society at a Time of Sweeping Change'. Proceedings, 1997 International Symposium, Jun. 20-21, 1997, pp. 118-124.

Martin, Anya, "Brighter Days Ahead", Assisted Living Today, vol. 9, Nov./Dec. 2002, pp. 19-22.

McCardle et al., "The Challenge of Utilizing New Technology in Design Education", Loughborough University, Idater 2000, 2000, pp. 122-127.

Meng et al., "E-Service Robot in Home Healthcare", Proceedings of the 2000 IEEE/RSJ, International Conference on Intelligent Robots and Systems, 2000, pp. 832-837.

Meiz, Cade, "HP Labs", available online at <http://www.pcmag.com/article2/0,2817,1130820,00.asp>, Jul. 1, 2003, 4 pages.

Michaud, Anne, "Introducing "Nursebot"", available online at <http://www.cs.cmu.edu/nursebot/web/press/globe 301/index.html>, 2001, 4 pages.

Microsoft Corporation, Inc., "Microsoft NetMeeting 3 Features excerpt from Official Microsoft NetMeeting 3.0 Book", available online at <http://technet.microsoft.com/en-us/library/cc723477.aspx>, 2012, 6 pages.

Minsky, Marvin, "Telepresence", OMNI Magazine, Jun. 1980, 6 pages.

Montemerlo, Reddy Whittaker, "Telepresence: Experiments in Next Generation Internet", available online at <http://www.ri.cmu.edu/creative/archives.htm>, Oct. 20, 1998, 3 pages.

Murphy, Robin R., "Introduction to AI Robotics", A Bradford Book, The MIT Press, Cambridge, Massachusetts, London, England, 2000, 487 pages.

Nakajima et al., "A Multimedia Teleteaching System using an Electronic Whiteboard for Two Way Communication of Motion Videos and Chalkboards", 2nd IEEE International Workshop on Robot and Human Communication, 1993, pp. 436-441.

Nakazato et al., "Group-Based Interface for Content-Based Image Retrieval", Proceedings of the Working Conference on Advanced Visual Interfaces, 2002, pp. 187-194.

Nakazato et al., "ImageGrouper: A Group-Oriented User Interface for Content-Based Image Retrieval and Digital Image Arrangement", Journal of Visual Languages & Computing, vol. 14, No. 4, Aug. 2003, pp. 45-46.

NERSC, "Berkeley Lab's RAGE Telepresence Robot Captures R&D100 Award", Available online at <https://www.nersc.gov/news-publications/news/nersc-center-news/2002/berkeley-lab-s-rage-telepresence-robot-captures-r-and-d100-award/>, Jul. 2, 2002, 2 pages.

Nomadic Technologies Inc., "Nomad XR4000 Hardware Manual", Release 1.0, Mar. 1999, 34 pages.

Noritsugu et al., "Application of Rubber Artificial Muscle Manipulator as a Rehabilitation Robot", Mechatronics, IEEE/ASME Transactions, vol. 2, No. 4, Dec. 1997, pp. 259-267.

North, Michael, "Telemedicine: Sample Script and Specifications for a Demonstration of Simple Medical Diagnosis and Treatment Using Live Two-Way Video on a Computer Network", Greenstar Corporation, 1998, 5 pages.

Ogata et al., "Development of Emotional Communication Robot: WAMOEBA-2R—Experimental Evaluation", Proceedings of the 2000 IEEE/RSJ International Conference on Intelligent Robots and Systems, vol. 1, 2000, pp. 175-180.

Ogata et al., "Emotional Communication Robot: WAMOEBA-2R—Emotion Model and Evaluation Experiments", Proceedings of the International Conference on Humanoid Robots, 2000, pp. 1-16.

Oh et al., "Autonomous Battery Recharging for Indoor Mobile Robots", Proceedings of Australian Conference on Robotics and Automation, 2000, pp. 1-6.

Ojha, Anand K., "An application of Virtual Reality in Rehabilitation", Proceedings of the 1994 IEEE Southeastcon 94. Creative Technology Transfer—A Global Affair, Apr. 1994, pp. 4-6.

Osborn, Jim, "Quality of Life Technology Center", QoLT Research Overview: A National Science Foundation Engineering Research Center, Carnegie Mellon University of Pittsburgh, 2 pages.

Panusopone et al., "Performance comparison of MPEG-4 and H.263+ for streaming video applications", Circuits Systems Signal Processing, vol. 20, No. 3, 2001, pp. 293-309.

Paulos et al., "A World Wide Web Telerobotic Remote Environment Browser", Available online at <http://www.w3.org/Conferences/WWW4/Papers/326/>, 1995, 15 pages.

Paulos et al., "Designing Personal Tele-Embodiment", Proceedings of IEEE International Conference on Robotics and Automation, vol. 4, May 16-20, 1998, pp. 3173-3178.

Paulos, Eric J., "Personal Tele-Embodiment", Dissertation, Doctor of Philosophy in Computer Science in the Graduate Division of the University of California at Berkeley, 2001, 282 pages.

Weiss et al., "Telework and Video-Mediated Communication: Importance of Real-Time, Interactive Communication for Workers with Disabilities", available online at <http://www.telbotics.com/research_3.htm>, retrieved on Nov. 23, 2010, 3 pages.

Zamrazil, Kristie, "Telemedicine in Texas: Public Policy Concerns", Focus Report, House Research Organization, Texas House of Representatives, No. 76-22, May 5, 2000, pp. 1-16.

Zipperer, Lorri, "Robotic Dispensing System", ISMP Medication Safety Alert!, vol. 4, No. 17, Aug. 25, 1999, 2 pages.

Zorn, Benjamin G., "Ubiquitous Telepresence", Department of Computer Science, University of Colorado, 1996, 13 pages.

Screenshot Showing Google Date for Lemaire Telehealth Manual, screenshot retrieved on Dec. 18, 2014, 1 page.

Appeal from the U.S District Court for the Central District of California in case No. 11-cv-9185, Judge Percy Anderson, Joint Appendix, vol. I of IV, Jun. 24, 2013, pp. A1-A6357.

Appeal from the U.S District Court for the Central District of California in case No. 11-cv-9185, Judge Percy Anderson, Joint Appendix, vol. II of IV, Jun. 24, 2013, pp. A6849-A10634.

Appeal from the U.S District Court for the Central District of California in case No. 11-cv-9185, Judge Percy Anderson, Joint Appendix, vol. III of IV, Jun. 24, 2013, pp. A10654-A15517.

Appeal from the U.S District Court for the Central District of California in case No. 11-cv-9185, Judge Percy Anderson, Joint Appendix, vol. IV of IV, Jun. 24, 2013, pp. A15677-A18127.

Appeal from the U.S. District Court for the Central District of California in No. 11-CV-9185, Judge Percy Anderson, May 9, 2014, pp. 1-48.

Civil Minutes—General: Case No. CV 11-9185PA (AJWx), *InTouch Tech., Inc. v. VGO Commons, Inc.*, Sep. 10, 2012, 7 pages.

Defendant VGO Communications, Inc.'s Invalidity Contentions Pursuant to the Feb. 27, 2012 Civil Minute Order, May 2, 2012, 143 pages.

Defendant-Counterclaimant VGO Communications, Inc.'s Supplemental Invalidity Contentions Pursuant to the Feb. 27, 2012 Civil Minute Order, May 14, 2012, 228 pages.

"Google translation of: Innovations Report", From research project to television star: Care-O-bot in ZDF series, available online at <http://www.innovations-report.de/specials/printa.php?id=5157>, Sep. 28, 2001, 2 pages.

(56) References Cited

OTHER PUBLICATIONS

"Magne Charge", Smart Power for Electric Vehicles, Aug. 26, 1997, 2 pages.
"More Online Robots: Robots that Manipulate", available online at <http://ford.ieor.berkeley.edu/ir/robots_a2.html>, Retrieved on Nov. 23, 2010, Aug. 2001, 2 pages.
"MPEG File Format Summary", available online at <http://www.fileformat.info/format/mpeg/egff.htm>, Feb. 1, 2001, 7 pages.
"Nomad Scout Language Reference Manual", Nomadic Technologies, Software Version 2.7, Part No. DOC00002, Jul. 12, 1999, 47 pages.
"Nomad Scout User's Manual", Nomadic Technologies, Software Version 2. 7, Part No. DOC00004, Jul. 12, 1999, pp. 1-59.
Opening Brief for Plaintiff-Appellant InTouch Technologies, Inc., Appeal from the U.S. District Court for the Central District of California in Case No. 11-cv-9185, Judge Percy Anderson, Apr. 12, 2013, 187 pages.
PictureTel Adds New Features and Functionality to Its Award-Winning Live200 Desktop Videoconferencing System, PR Newswire Association, LLC, Gale, Cengage Learning, Jun. 13, 1997, 4 pages.
Reply Brief for Defendant-Appellee VGO Communications, Inc., Appeal from the U.S. District Court for the Central District of California, in Case No. 2:11-cv-9185, Judge Percy Anderson, May 28, 2013, 75 pages.
Reply Brief for Plaintiff-Appellant InTouch Technologies, Inc., Appeal from the U.S. District Court for the Central District of California in Case No. 11-cv-9185, Judge Percy Anderson, Jun. 14, 2013, 39 pages.
"Robart I, II, III", Spawar, Systems Center Pacific, 1998, 8 pages.
Using your Infrared Cell Phone Camera, available online at <http://www.catsdomain.com/xray/about.htm>, Courtesy of Internet Wayback Machine, Jan. 30, 2010, 4 pages.
Ivanova, Natali, "Master's Thesis: Internet Based Interface for Control of a Mobile Robot", Department of Numerical Analysis and Computer Science, 2003, 59 pages.
Jacobs et al., "Applying Telemedicine to Outpatient Physical Therapy", AMIA, Annual Symposium Proceedings, 2002, 1 page.
Jenkins et al., "Telehealth Advancing Nursing Practice", Nursing Outlook, vol. 49, No. 2, Mar. 2001, pp. 100-105.
Johanson, Mathias, "Supporting Video-Mediated Communication Over the Internet", Department of Computer Engineering, Chalmers University of Technology, Gothenburg, Sweden, 2003, 222 pages.
ACM Digital Library Record, "Autonomous Robots vol. 11 Issue 1", available online at <http://dl.acm.org/citation.cfm?id=591550&picked=prox&cfid=360891374&cftoken=35225929>, Jul. 2001, 2 pages.
Active Media, Inc., "Saphira Software Manual", Saphira Version 5.3, 1997, 105 pages.
Activmedia Robotics, "Pioneer 2/PeopleBot TM", Operations Manual, Version 9, Oct. 2001, 78 pages.
Adams, Chris, "Simulation of Adaptive Behavior (SAB'02)", Mobile Robotics Research Group, The Seventh International Conference, retrieved on Jan. 22, 2014, available online at <http://www.dai.ed.ac.uk/groups/mrg/MRG.html>, Aug. 4-11, 2002, 1 page.
Ando et al., "A Multimedia Self-service Terminal with Conferencing Functions", Robot and Human Communication, Tokyo, Proceedings of 4th IEEE International Workshop, Jul. 5-7, 1995, pp. 357-362.
Android Amusement Corp., "What Marketing Secret Renting Robots from Android Amusement Corp!", (Advertisement), 1982, 1 page.
Apple Inc., "I Phone", iPhone Series, XP002696350, Sep. 21, 2012, pp. 1-29.
Applebome, Peter, "Planning Domesticated Robots for Tomorrow's Household", New York Times, available online at <http://www.theoldrobots.com/images17/dc17.jpg>, Mar. 4, 1982, pp. 21 and 23.
Bar-Cohen et al., "Virtual Reality Robotic Telesurgery Simulations Using MEMICA Haptic System", Proceedings of SPIE's 8th Annual International Symposium on Smart Structures and Materials, Mar. 5-8, 2001, pp. 1-7.

Barrett, Rick, "Video Conferencing Business Soars as Companies Cut Travel; Some Travel Cuts Are Permanent", available online at <http://www.ivci.com/international_videoconferencing_news_videoconferencing_news_19.html>, May 13, 2002, 2 pages.
Bartholomew, "Pharmacy Apothecary", available online at <http://classes.bnf.fr/ema/grands/034.htm>, retrieved an Jul. 26, 2012, 2 pages.
Bauer et al., "Remote Telesurgical Mentoring: Feasibility and Efficacy", IEEE, Proceedings of the 33rd Hawaii International Conference on System Sciences, 2000, pp. 1-9.
Bauer, Jeffrey C., "Service Robots in Health Care: The Evolution of Mechanical Solutions to Human Resource Problems", Bon Secours Health System Inc., Technology Early Warning System(TEWS), Future of Service Robots in Health Care, Jun. 2003, pp. 1-10.
Bischoff, Rainer, "Design Concept and Realization of the Humanoid Service Robot HERMES", Field and Service Robotics, Springer, 1998, pp. 485-492.
Blackwell, Gerry, "Video: A Wireless LAN Killer App?", available online at <http://www.wi-fiplanet.com/columns/article.php/1010261/Video-A-Wireless-LAN-Killer>, Apr. 16, 2002, 4 pages.
Blaer et al., "TopBot: Automated Network Topology Detection With a Mobile Robot", IEEE, Proceedings of the 2003 International Conference on Robotics 7 Automation, Taipei, Taiwan, Sep. 14-19, 2003, pp. 1582-1587.
Bradner, S., "The Internet Standards Process—Revision 3", Network Working Group, Request for Comments: 2026, BCP: 9, Obsoletes: 1602, Category: Best Current Practice, Oct. 1996, pp. 1-36.
Brenner, Pablo, "A technical tutorial on the IEEE 802.11 protocol", Breezecom Wireless Communications, 1997, pp. 1-24.
Breslow et al., "Effect of a Multiple-Site Intensive Care Unit Telemedicine Program on Clinical and Economic Outcome an Alternative Paradigm for Intensivist Staffing", Critical Care Med, vol. 32, No. 1, Jan. 2004, pp. 31-38.
Brooks, Rodney, "A Robust Layered Control System for a Mobile Robot", IEEE, Journal of Robotics and Automation, vol. 2, No. 1, Mar. 1986, pp. 14-23.
Brooks, Rodney Allen, "Remote Presence", Abstracts from Flesh & Machines, How Robots Will Change Us, Feb. 2002, pp. 131-147.
Celi et al., "The eICU: It's Not Just Telemedicine", Critical Care Medicine vol. 29, No. 8 (Supplement), Aug. 2001, pp. 183-189.
Cheetham et al., "Interface Development for a Child's Video Conferencing Robot", available online at <www.ryerson.ca/pebbles/publications/paper-iea200hfes-last.pdf>, 2000, 4 pages.
Christensen et al., "BeeSoft User's Guide and Reference", Robots for the Real World™, Real World Interface, Inc , Sep. 26, 1997, 203 pages.
Shu et al., "Detection of Target Mobile Signal Strength", Technical Development, Motorola Inc, Jan. 1999, pp. 205-206.
Paulos et al., "Social Tele-Embodiment Understanding Presence", Autonomous Robots, vol. 11, Issue 1, Kluwer Academic Publishers, Jul. 2001, pp. 87-95.
Paulos et al., "Ubiquitous Tele-Embodiment Applications and Implications", International Journal of Human Computer Studies, vol. 46, No. 6, Jun. 1997, pp. 861-877.
Paulos, Eric John Canny, "Video of PRoP 2 at Richmond Field Station", www.prop.org Printout of Home Page of Website and two-page Transcript of the audio portion of said PRoP Video, May 2001, 2 pages.
PictureTel Corporation, "PictureTel Live200 for Windows NT Product Guide", 1997, 63 pages.
Pin et al., "A New Family of Omnidirectional and Holonomic Wheeled Platforms for Mobile Robots", IEEE Transactions on Robotics and Automation, vol. 10, No. 4, Aug. 1994, pp. 480-489.
Piquepaille, Roland, "This Blog and its RSS Feed Are Moving", Roland Piquepaille's Technology Trends, How new technologies are modifying our way of life, Oct. 31, 2004, 2 pages.
West et al., "Design of Ball Wheel Mechanisms for Omnidirectional Vehicles with Full Mobility and Invariant Kinematics", Journal of Mechanical Design, vol. 119, Jun. 1997, pp. 153-161.
Yamasaki et al., "Applying Personal Robots and Active Interface to Video Conference Systems", 6th International Conference on Human Computer Interaction, vol. B, 1995, pp. 243-248.

(56) References Cited

OTHER PUBLICATIONS

Yamauchi, Brian, "PackBot: A Versatile Platform for Military Robotics", Proceedings of SPIE for Military Robotics, 2004, pp. 228-237.

Yong et al., "Robot Task Execution with Telepresence Using Virtual Reality Technology", 1998 International Conference on Mechatronic Technology, Nov. 30-Dec. 2, 1998, pp. 1-8.

Zambroski, James, "CMU, Pitt Developing 'Nursebot'", available online at <http://www.cs.cmu.edu/~nursebot/web/press/tribunereview.html>, Oct. 27, 2000, 3 pages.

Radvision, "Making Sense of Bandwidth the Netsense Way", Network Congestion in Unmanaged Networks Bandwidth Estimation and Adaptation Techniques, White Paper, Radvision's Netsense Technology, 2010, 7 pages.

Reynolds et al., "Review of Robotic Telemedicine Utilization in Intensive Care Units (ICUs)", 11th Annual ATA Symposium, Tampa, Florida, 2011, 1 page.

Roach, Adam, "Automatic Call Back Service in SIP", Internet Engineering Task Force, Internet Draft, Category: Informational, Mar. 2000, 8 pages.

Rovetta et al., "A New Telerobotic Application: Remote Laparoscopic Surgery Using Satellites and optical fiber Networks for Data Exchange", International Journal of Robotics Research, vol. 15, No. 3, Jun. 1, 1996, pp. 267-279.

Roy et al., "Towards Personal Service Robots for the Elderly", Workshop on Interactive Robots and Entertainment (WIRE 2000), available online at <http://www.ri.cmu.edu/pb_files/pub2/roy_nicholas_2000_1/roy_nicholas_2000_1.pdf>, vol. 25, Apr. 30-May 1, 2000, 7 pages.

Sachs et al., "Virtual Visit: Improving Communication for Those Who Need it Most", Studies in Health Technology and Informatics, vol. 94, Medicine Meets Virtual Reality 11,2003, pp. 302-308.

Salemi et al., "MILO: Personal Robot Platform", IEEE/RSJ International Conference on Intelligent Robots and Systems, Aug. 2005, pp. 4089-4094.

Sandt et al., "Perceptions for a Transport Robot in Public Environments", Proceedings of the 1997 IEEE/RSJ International Conference on Intelligent Robots and Systems, vol. 1, Sep. 7-11, 1997, pp. 360-365.

Sawyer, Robert J., "Inventing the Future: 2000 Years of Discovery", available online at <http://www.sfwriter.com/pritf.htm>, Jan. 2, 2000, 2 pages.

Schaeffer et al., "Care-O-BotTM: The Concept of a System for Assisting Elderly or Disabled Persons in Home Environments", Proceedings of the 24th Annual Conference of the IEEE Industrial Electronics Society, vol. 4, 1998, pp. 2476-2481.

Schraft et al., "Care-O-bot™: The Concept of a System for Assisting Elderly or Disabled Persons in Home Environments", IEEE Proceedings of the 24th Annual Conference of the Industrial Electronics Society, IECON '98, Aug. 31-Sep. 4, 1998, pp. 2476-2481.

Schultz et al., "Web Interfaces for Mobile Robots in Public Places", IEEE Robotics & Automation Magazine, vol. 7, No. 1, Mar. 2000, pp. 48-56.

Shimoga et al., "Touch and Force Reflection for Telepresence Surgery", Proceedings of the 16th Annual Internationa Conference of the IEEE Engineering in Medicine and Biology Society, Nov. 1994, pp. 1049-1050.

Siegwart et al., "Interacting Mobile Robots on the Web", Proceedings of the 1999 IEEE International Conference on Robotics and Automation, May 1999, pp. 1-7.

Simmons et al., "Xavier: An Autonomous Mobile Robot on the Web", IEEE Robotics and Automation Magazine, 1999, pp. 43-48.

Stephenson, Gary, "Dr. Robot Tested at Hopkins", available online at <http://www.hopkinsmedicine.org/press/2003/august/030805.htm>, Aug. 5, 2003, 2 pages.

Stoianovici et al., "Robotic Tools for Minimally Invasive Urologic Surgery", Complications of Urologic Laparoscopic Surgery: Recognition, Management and Prevention, Dec. 2002, 17 pages.

Suplee, Curt, "Mastering the Robot", The Washington Post, Washington Post Staff Writer, Sep. 17, 2000, 5 pages.

Tahboub et al., "Dynamics Analysis and Control of a Holonomic Vehicle With Continuously Variable Transmission", Transactions of the ASME, Journal of Dynamic Systems, Measurement and Control, vol. 124, Mar. 2002, pp. 118-126.

Telepresence Research, Inc., "The Telepresence Mobile Robot System", available online at <http://www.telepresence.com/telepresence-research/TELEROBOT/>, Feb. 20, 1995, 3 pages.

Tendick et al., "Human-Machine Interfaces for Minimally Invasive Surgery", Proceedings of the 19th Annual International Conference of the IEEE Engineering in Medicine and Biology Society, vol. 6, Oct. 30-Nov. 2, 1997, pp. 2771-2776.

Theodosiou et al., "MuLVAT: A Video Annotation Tool Based on XML-Dictionaries and Shot Clustering", 19th International Conference, Artificial Neural Networks—ICANN 2009, Part II, Sep. 14-17, 2009, pp. 913-922.

Thrun et al., "Probabilistic Algorithms and the Interactive Museum Tour-Guide Robot Minerva", International Journal of Robotics Research, vol. 19, 2000, pp. 1-35.

Time, Lists, "Office Coworker Robot", Best Inventions of 2001, available online at <http://content.time.com/time/specials/packages/article/0,28804,1936165_1936255_1936640,00.html>, Nov. 19, 2001, 2 pages.

Tipsuwan et al., "Gain Adaptation of Networked Mobile Robot to Compensate QoS Deterioration", 28th Annual Conference of the Industrial Electronics Society, vol. 4, Nov. 5-8, 2002, pp. 3146-3151.

Tsui et al., "Exploring Use Cases for Telepresence Robots", 6th ACM/IEEE International Conference on Human-Robot Interaction (HRI), Mar. 2011, pp. 11-18.

Tyrrell et al., "Teleconsultation in Psychology: The Use of Videolinks for Interviewing and Assessing Elderly Patients", Age and Ageing, vol. 30, No. 3, May 2001, pp. 191-195.

Tzafestas et al., "VR-Based Teleoperation of a Mobile Robotic Assistant: Progress Report", Technical Report DEMO 2000/13, Institute of Informatics and Telecommunications, National Center for Scientific Research "Demokritos", Nov. 2000, pp. 1-23.

UMASS Lowell Robotics Lab, "Robotics Lab @ UMASS Lowell", Brochure, 2011, 2 pages.

Urquhart, Kim, "InTouch's Robotic Companion 'Beams Up' Healthcare Experts", Medical Device Daily, vol. 7, No. 39, Feb. 27, 2003, pp. 1, 4.

Video Middleware Cookbook, "H.350 Directory Services for Multimedia", 2 pages.

Weaver et al., "Monitoring and Controlling Using the Internet and Java", Proceedings of the 25th Annual Conference of the IEEE Industrial Electronics Society, vol. 3, 1999, pp. 1152-1158.

Weiss et al., "Pebbles: A Personal Technology for Meeting Education, Social and Emotional Needs of Hospitalised Children", Personal and Ubiquitous Computing, vol. 5, No. 3, Aug. 2001, pp. 157-168.

Cleary et al., "State of the Art in Surgical Robotics: Clinical Applications and Technology Challenges", Feb. 24, 2002, pp. 1-26.

CMU Course 16×62, "Robot user's manual", (describing the Nomad Scout), Carnegie Mellon University, Feb. 1, 2001, 11 pages.

CNN, "Floating 'Droids' to Roam Space Corridors of the Future", Available online at <http://edition.cnn.com/2000/TECH/space/01/12/psa/>, Jan. 12, 2000, 3 pages.

cnn.com, "Paging Dr.Robot: Machine Helps Doctors with Patients", Sep. 30, 2003, 3 pages.

Crowley, Susan L., "Hello to Our Future", AARP Bulletin, Jan. 2000, 12 pages.

Dalton, Barnaby, "Techniques for Web Telerobotics", PhD Thesis, University of Western Australia, 2001, 243 pages.

Dario et al., "A Robot Workstation for Diagnosis and Physical Therapy", IEEE Catalog No. 88TH0234-5, 1989, pp. 67-72.

Davies, Brian, "Robotics in Minimally Invasive Surgery", IEE Colloquium on Through the Keyhole: Microengineering in Minimally Invasive Surgery, 1995, pp. 1-2.

Davis, Erik, "Telefriend, Meet iRobot, The Smartest Webcam on Wheels", Wired Magazine, Issue 8.09, Available online at <http://www.wired.com/wired/archive/8.09/irobot.html?pg=1&topic=&topic_set=>, Sep. 2000, 3 pages.

(56) References Cited

OTHER PUBLICATIONS

Dean et al., "1992 AAAI Robot Exhibition and Competition", Articles, AI Magazine, vol. 14, No. 1, 1993, 15 pages.
Digiorgio, James, "Is Your Emergency Department of the Leading Edge?", Chicago Hospital News, vol. 2, No. 12, 2005, 3 pages.
Dudenhoeffer et al., "Command and Control Architectures for Autonomous Micro-Robotic Forces", FY00 Project Report, Idaho National Engineering and Environmental Laboratory Human Systems Engineering and Sciences Department, Idaho Falls, Apr. 2001, 43 pages.
Elhajj et al., "Real-Time Haptic Feedback in Internet-Based Telerobotic Operation", IEEE International Conference on Electro/Information Technology, available online at <http://www.egr.msu.edu/~ralab-web/cgi_bin/internet-teleoperation.php>, Jun. 2000, 10 pages.
Elhajj et al., "Supermedia in Internet-Based Telerobotic Operations", Management of Multimedia on the InternetLecture Notes in Computer Science, Springer-Verlag Berlin Heidelberg, vol. 2216, Oct. 29-Nov. 1, 2001, pp. 359-372.
Elhajj et al., "Synchronization and Control of Supermedia Transmission via the Internet", Proceedings of 2001 International Symposium on Intelligent Multimedia Video and Speech Processing, May 2-4, 2001, pp. 320-323.
Ellison et al., "Telerounding and Patient Satisfaction Following Surgery", vol. 199, No. 4, Oct. 2004, pp. 523-530.
Evans et al., "The Trackless Robotic Courier", PYXIS HelpMate®, 2007, 3 pages.
Fels et al., "Developing a Video-Mediated Communication System for Hospitalized Children", Telemedicine Journal, vol. 5, No. 2, 1999, 30 pages.
Fetterman et al., "Videoconferencing Over the Internet", 2001, 8 pages.
Fiorini et al., "Health Care Robotics: A Progress Report", IEEE International Conference on Robotics and Automation, Apr. 20-25, 1997, pp. 1271-1276.
Fong, Terrence, "Collaborative Control: A Robot-Centric Model for Vehicle Teleoperation", Doctoral Dissertation, Technical Report CMU-RI-TR-01-34, Robotics Institute, Carnegie Mellon University, Nov. 2001, 197 pages.
Fulbright et al., "SWAMI: An Autonomous Mobile Robot for Inspection of Nuclear Waste of Storage Facilities", Autonomous Robots, vol. 2, 1995, pp. 225-235.
Gaidioz et al., "Synchronizing Network Probes to Avoid Measurement Intrusiveness with the Network Weather Service", Proceedings of the Ninth International Symposium on High-Performance Distributed Computing, 2000, pp. 147-154.
Garner et al., "The Application of Telepresence in Medicine", BT Technology Journal, vol. 15, No. 4, Oct. 1, 1997, pp. 181-187.
Ghiasi et al., "A Generic Web-based Teleoperations Architecture: Details and Experience", Proceedings of SPIE, Telemanipulator and Telepresence Technologies VI, vol. 3840, No. 234, Sep. 19, 1999, 14 pages.
Goldberg et al., "Collaborative Teleoperation via the Internet", IEEE International Conference on Robotics and Automation (ICRA), vol. 2, 2000, pp. 2019-2024.
Goldberg et al., "Desktop Teleoperation via the World Wide Web", IEEE International Conference on Robotics and Automation, vol. 1, May 21-27, 1995, pp. 654-659.
Goldenberg et al., "Telemedicine in Otolaryngology", American Journal of Otolaryngology, vol. 23,No. 1, 2002, pp. 35-43.
Goldman, Lea, "Machine Dreams", available online at <http://www.forbes.com/global/2002/0527/043.html>, May 27, 2002, 5 pages.
Gostai, "Gostai Jazz: Robotic Telepresence", available online at <http://www.robotshop.com/media/files/pdf/gostai-jazz-information-sheet.pdf>, 4 pages.
Gump, Michael D., "Robot Technology Improves VA Pharmacies", U.S. Medicine Informational Central, Jul. 2001, 3 pages.
Al-Kassab et al., "A Review of Telemedicine", Journal of Telemedicine and Telecare, vol. 5, Supplement 1, 1999, pp. 103-106.
Han et al., "Construction of an Omnidirectional Mobile Robot Platform Based on Active Dual-Wheel Caster Mechanisms and Development of a Control Simulator", Journal of Intelligent and Robotic Systems, vol. 29, Issue 3, Nov. 2000, pp. 257-275.
Handley et al., "RFC 2327—SDP: Session Description Protocol", available online at <http://www.faqs.org/rfcs/rfc2327.html>, Apr. 1998, 22 pages.
Hanebeck et al., "Roman: A Mobile Robotic Assistant for Indoor Service Applications", IEEE/RSJ International Conference on Intelligent Robots and Systems, vol. 2, Sep. 7-11, 1997, pp. 518-525.
Harmo et al., "Moving Eye-Interactive Telepresence Over Internet With a Ball Shaped Mobile Robot", available online at <http://automation.tkk.fi/files/tervetaas/MovingEye4.pdf>, 2000, 6 pages.
Haule et al., "Control Scheme for Delayed Teleoperation Tasks", IEEE Pacific Rim Conference on Communications, Computers, and Signal Processing, May 17-19, 1995, pp. 157-160.
Hees, William P., "Communications Design for a Remote Presence Robot", CSCI E-131b, Final Project, Jan. 14, 2002, 12 pages.
Herias et al., "Flexible Virtual and Remote Laboratory for Teaching Robotics", Current Developments in Technology-Assisted Education, Jun. 2006, pp. 1959-1963.
Holmberg et al., "Development of a Holonomic Mobile Robot for Mobile Manipulation Tasks", International Journal of Robotics Research, vol. 19, No. 11, Nov. 2000, pp. 1066-1074.
Ishiguro et al., "Integrating a Perceptual Information Infrastructure with Robotic Avatars: A Framework for Tele-Existence", IEEE/RSJ International Conference on Intelligent Robots and Systems, vol. 2, 1999, pp. 1032-1038.
Ishihara et al., "Intelligent Microrobot DDS (Drug Delivery System) Measured and Controlled by Ultrasonics", Intelligent Robots and Systems '91. 'Intelligence for Mechanical Systems, IEEE/RSJ International Workshop, vol. 2, Nov. 3-5, 1991, pp. 1145-1150.
ITU, "Call Completion Supplementary Services for H.323", ITu-T, Telecommunication Standardization Sector of ITU, H.450.9, Series H: Audiovisual and Multimedia Systems, Nov. 2000, 63 pages.
ITU, "Call Intrusion Supplementary Service for H.323", ITU-T, Telecommunication Standardization Sector of ITU, H.450.11, Series H: Audiovisual and Multimedia Systems, Mar. 2001, 59 pages.
ITU, "Packet-Based Multimedia Communications Systems", ITU-T, Telecommunication Standardization Sector of ITU, H.323, Series H: Audiovisual and Multimedia Systems, Feb. 1998, 128 pages.
ITU, "Transmission of Non-Telephone Signals: A Far End Camera Control Protocol for Videoconferences Using H.224", ITU-T, Telecommunication Standardization Sector of ITU, H.281, Nov. 1994, 12 pages.
Paulos, Eric John, "Personal Tele-Embodiment", OskiCat Catalog Record, UCB Library Catalog, 2001, 3 pages.
Paulos et al., "Personal Tele-Embodiment", Chapter 9 in Goldberg, et al., ed. "Beyond webcams", MIT Press, Jan. 4, 2002, pp. 155-167.
Paulos, Eric John, "Personal Tele-Embodiment", Introductory and cover pages from 2001 Dissertation including Contents table, together with e-mails relating thereto from UC Berkeley Libraries, as shelved at UC Berkeley Engineering Library (Northern Regional library Facility), May 8, 2002, 25 pages (including 4 pages of e-mails).
Paulos et al., "PRoP: Personal Roving Presence", ACM:CHI Proceedings of CHI '98, 1998, 8 pages.

* cited by examiner

CONNECTIVITY INFRASTRUCTURE FOR A TELEHEALTH PLATFORM

CROSS-REFERENCE TO RELATED APPLICATIONS

This application claims priority to U.S. provisional application No. 62/550,514, filed Aug. 25, 2017, the contents of which are hereby incorporated by reference.

TECHNICAL FIELD

The present technology pertains to telehealth systems, and more specifically to a network and connectivity infrastructure for a telehealth platform.

BACKGROUND

Telehealth or telemedicine is the practice of conducting consultations between patients and caregivers in different locations. Telemedicine technologies allow physicians and other care providers to see, hear, communicate with, diagnose, instruct or otherwise provide care to remotely located patients. Existing telemedicine technologies range from simple audio communication devices such as telephones to videoconferencing systems to remotely controlled mobile videoconferencing devices with autonomous navigation capabilities. One such remotely controlled device is that marketed under the trademark RP-VITA or INTOUCH VITA by INTOUCH TECHNOLOGIES, INC. of Goleta, Calif. Other telemedicine devices or "endpoints" offered by INTOUCH TECHNOLOGIES, INC., include the cart-based INTOUCH LITE, INTOUCH VICI, and INTOUCH VANTAGE, the portable INTOUCH EXPRESS and INTOUCH VIEWPOINT or VIEWPOINT TABLET, and the ultra-portable INTOUCH TV, which can be coupled to any television to create a telemedicine endpoint. In addition, any computing device running INTOUCH VIEWPOINT software or a web browser directed to the INTOUCH cloud-based CONSUMER portal can be used to conduct a telemedicine session.

Each of these devices, which are typically situated in the vicinity of a patient, includes at least one camera, monitor, microphone, and speaker that enable two-way audiovisual communication between the patient and the remote physician. In conjunction with a managed network, cloud-based documentation platform, and a purpose-built user interface provided to the physician via a laptop, desktop, or smartphone, these devices allow physicians to communicate with, examine, and diagnose even high-acuity patients from a remote location, as well as retrieve, edit, and store patient medical records and medical imaging from disparate healthcare facility IT systems and electronic health record systems.

Many organizations that wish to offer telehealth services struggle to establish a delivery platform that is both secure and reliable but also flexible and scalable. Complex webs of Virtual Private Networks (VPNs) may provide secure communications among care locations within a healthcare organization, but VPNs tend to suffer from reliability issues that may prevent or otherwise interrupt telehealth sessions at critical times. Moreover, pre-established VPNs generally do not permit sessions with entities outside of the organization that administers the VPN. This may prevent or hinder the ability of an external specialist to join and contribute to a session where his or her expertise may be helpful.

SUMMARY OF THE CLAIMED SUBJECT MATTER

One aspect of the disclosure is a telehealth system comprising a public communications network (PCN), a plurality of provider access devices coupled to the PCN, and a plurality of patient access devices that can be controlled by any of the plurality of provider access devices. The plurality of patient access devices includes a first patient access device at a first location coupled to the PCN via a first local area network (LAN) and a first firewall and a second patient access device at a second location coupled to the PCN via a second LAN and a second firewall. The system also includes a monitoring server coupled to the PCN. The monitoring server receives status information from the plurality of patient access devices, wherein the status information includes presence information indicating the availability of the patient access device to participate in a communication session and device status of the patient access device. The system may also include a connectivity server coupled to the PCN. The connectivity server includes a database of connectivity rules, each connectivity rule including an identification of a healthcare provider and a location of patient access device the healthcare provider is authorized to access. The system may also include a plurality of geographically dispersed communications servers coupled to the PCN. Each of the plurality of communication servers has a network address on the PCN and is configured to establish a two-way audio/video communication session between one of the provider access devices and one of the patient access devices. At least one of the plurality of communications servers receives and maintains at least a portion of the database of connectivity rules from the connectivity server and the first communication firewall and the second communication firewall are configured to allow incoming communications from the network addresses of at least one of the plurality of communication servers. The provider access device transmits the identification of a healthcare provider to the communications server and receives from the communications server a list of patient access device locations that the healthcare provider is authorized to access and a status of each patient access device at each of the received locations. The provider access device receives a selection of a patient access device location from the healthcare provider and communicates the selected location to an optimal one of the plurality of communications servers. The optimal communications server establishes a communication session between the provider access device and the patient access device at the selected location. In addition, the monitoring server stores information regarding the established communication session in a reporting database.

DETAILED DESCRIPTION

Figure 1:
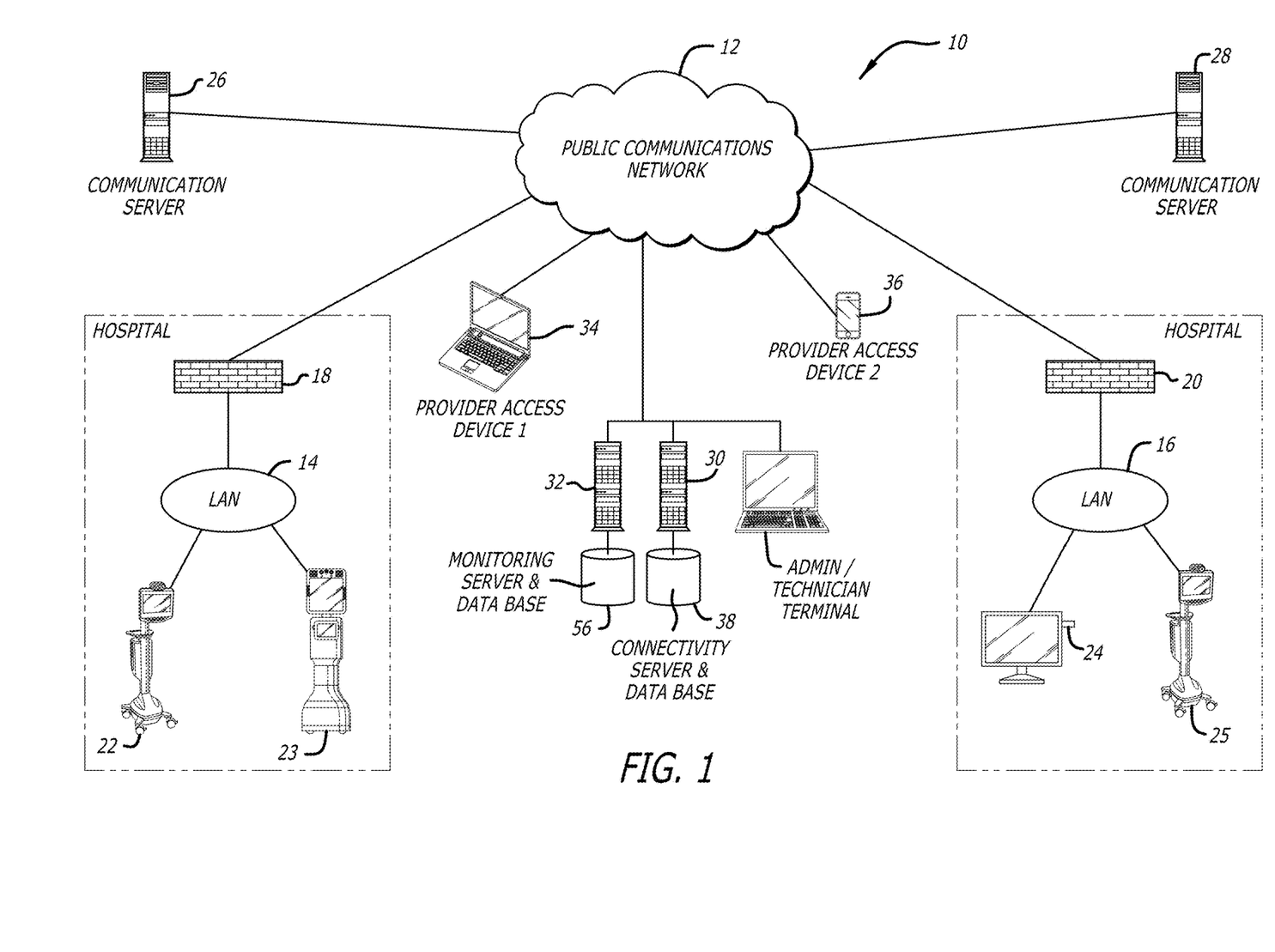
FIG. 1 illustrates an exemplary telehealth platform.

FIG. 1 illustrates an example of a telehealth platform 10. The platform may include a public communications network (PCN) 12, such as the Internet, that connects numerous local-area networks (LANs) 14, 16. Each LAN 14, 16 may be coupled to the PCN 12 via a communications firewall 18, 20. One or more patient access devices 22-25 may be coupled to each LAN 14, 16. A patient access device may also be coupled to the PCN 12 via a wide-area network (WAN), such as a cellular communications network (not shown). The platform may include a plurality of communications servers 26, 28, a connectivity server 30, and a monitoring server 32 coupled to the PCN. The platform may also include one or more provider access devices 34, 36 coupled to the PCN via a LAN or WAN (not shown). In general, the platform allows a physician or other healthcare provider to provide care to a patient by establishing a two-way audio/video communication between a patient access device 22-25 and a provider access device 34, 36. Although patient access devices 22-25 and provider access devices 24, 26 may be discussed as distinct and/or purpose-built devices, it is to be appreciated that the platform accommodates connections between generic users and/or devices.

Each LAN 14, 16 may be associated with a medical facility, such as a hospital, clinic, surgery center, primary care facility, ambulatory care center, or nursing home. A LAN could also be associated with a patient's home and/or the home or office of a care provider, such as a physician, clinician, nurse, or caretaker. For larger organizations, a LAN could take the form of a wide-area network (WAN) that connects multiple LANs. The LAN or WAN associated with each medical facility may also employ or otherwise support one or more virtual private networks (VPNs). However, the managed network architecture of the platform 10 generally eliminates the need for VPNs.

Each LAN 14, 16 may be coupled to the public communications network 12 via a firewall 18, 20. Each firewall 18, 20 may be configured by an administrator to allow incoming connections from one or more IP addresses representing the IP addresses of one or more of the communication servers 26, 28, the monitoring server 32, and/or the connectivity server 34. For example, the administrator may be provided with a list of trusted IP addresses and/or port numbers associated with the telehealth platform 10 and configure the firewall 18, 20 to accept connections from these IP addresses and/or ports.

An exemplary patient access device 22-25 may take the form of any device that allows the user of the provider access device to see and hear the patient. Preferably, the patient access device also allows the patient to see and hear the provider. In one embodiment, a patient access device may take the form of a telemedicine cart 22, 25 including a camera, a monitor, a microphone, and a speaker. In another embodiment, a patient access device could be a mobile telepresence robot 23 that includes a camera, a monitor, a microphone, and a speaker, as well as a mobile base that can be controlled by the remote healthcare provider using the provider access device. In yet another embodiment, the patient access device 24 could take the form of a small form factor computing device that executes a patient access device software program and is coupled to a camera, a monitor, a microphone, and a speaker via input/output ports on the computing device. One such small form factor computing device is the COMPUTE STICK, manufactured by INTEL Corporation. Alternatively, the patient access device may take the form of videoconferencing enabled tablet, smartphone, or laptop or desktop computer executing a patient access device software program. Additional examples of patient access devices include INTOUCH VITA, INTOUCH LITE, INTOUCH VANTAGE, INTOUCH XPRESS, INTOUCH VICI, and INTOUCH TV, all marketed by INTOUCH TECHNOLOGIES, INC., of Goleta, Calif. The details of various examples of provider access devices may be found in the follow U.S. patent and application publication numbers, the contents of which are hereby incorporated by reference: U.S. Pat. Nos. 6,925,357; 7,158,859; 8,515,577; 8,670,017; 8,718,837; 8,996,165; 9,198,728; 2009/0240371; and 2011/0213210.

An exemplary provider access device 34, 36 may take the form of any laptop or desktop computer, tablet, smartphone, or videoconferencing device including a camera, a monitor, a microphone, and a speaker. The provider access device may include a provider access software program that, when launched, provides an integrated application and user interface for accessing, controlling, or otherwise communicating with patient access devices 22-25 in order to treat a patient remotely. In addition, the provider access software may include the ability to launch a clinical documentation tool the physician can use to document the patient encounter, either within the provider access interface or within a separate application window launched from within the provider access software interface. The clinical documentation tool may be integrated with a hospital medical records system. The provider access software may also allow the provider to retrieve and view medical images of the patient, such as PACS images from MRIs or CT scans that have been performed on the patient. The provider access software may allow the provider to view these images within the application window of the provider access software or within a separate application window launched from within the provider access software interface.

In an alternative embodiment, the provider access device 34, 36 may simply employ a web browser that the user directs to a URL having a web-based provider access software application. This embodiment avoids the need to have a native application installed on the provider access device.

In yet another embodiment, both platform 10 may include a cloud-based telehealth portal configured to host telehealth sessions between any videoconferencing enabled devices via web browsers directed to and authenticated with the telehealth portal.

In general, the provider access software interface may include a variety of layouts and features as described in the following U.S. patent and application publication numbers, the contents of which are hereby incorporated by reference: U.S. Pat. Nos. 8,179,418; 8,849,680; 9,361,021; 9,098,611; 2005/0204438; and 2006/0052676. In addition, the provider access software interface may be customized depending on the type of patient access device the user chooses to connect to, as described in U.S. Pat. No. 8,897,920, the contents of which are hereby incorporated by reference.

The platform may include one or more geographically dispersed communications servers 26, 28 coupled to the public communications network 12. An exemplary communication server may operate as a session initiation protocol (SIP) server or similar protocol for signaling and controlling multimedia communication session over the internet. Each of the communications server 26, 28 is configured to facilitate a multimedia communication sessions between a provide access device 34, 36 and a patient access device 22-25 and/or to facilitate communication between a patient or provider access device and other servers coupled to the PCN, or between other servers themselves. The other servers could include another communications server, the monitoring server 32, the connectivity server 30, an authentication server, a medical records server, a billing server, a reporting server, or the like. In a platform with multiple, geographically dispersed communications servers 26, 28, an optimal server to facilitate a session between a provider access device 34, 36 and a patient access device 22-25 may be selected based on server load and/or network conditions such as latency, available link bandwidth, and/or round-trip time.

The connectivity server 30 maintains a database 38 of connectivity rules that control access throughout the platform. Each connectivity rule may specify a user and a location. A user may correspond to a medical care provider. A location in this context is a unique identifier that may represent the name of the location of a specific patient access device. For example, if the device is the only patient access device located in the emergency department of Mercy General Hospital in Asheville, N.C., the location may be named "Mercy General, Ashville, ED." A connectivity rule may indicate that a "Dr. Jim Norris" can connect to or otherwise access the patient access device located at "Mercy General, Ashville, ED." The location may be distinct and/or decoupled from the name of the hospital or facility, the customer, the physical location of the device (in terms of latitude and longitude), and/or the device ID or serial number.

The database 38 of connectivity rules may be maintained by an administrator via a web portal that allows the administrator to add, delete, or otherwise modify connectivity rules. For example, when a new doctor is registered and obtains an account on the telehealth platform 10, one or more connectivity rules may be added to the database 38, with each rule specifying the doctor's username and a patient access device location he or she is authorized to access. A single provider may have access to numerous patient access devices located throughout one or more hospitals, hospital networks, or other care locations. In such cases, the database 38 may include a separate rule for each patient access device location the provider is authorized to access. In other embodiments, a single connectivity rule for a provider could specify a group of patient access devices the provider is authorized to access. A provider may not be able to connect to a patient access device location if there is no corresponding connectivity rule associating the provider with the patient access device.

In one embodiment, connectivity between users and locations may be grouped or otherwise managed according to "programs" maintained in the connectivity database 38. A program may be a unique name representing a set of users that have access to the devices at a set of locations for a particular purpose. For example, a major hospital with several neurologists on staff may contract with several smaller hospitals in remote locations to provide stroke tele-consults at the remote locations. Once telehealth endpoints are installed or otherwise made available at the remote hospitals, a program may be created in the database that includes the neurologists at the major hospital in the users list and the locations of the telehealth devices at each of the remote hospitals in the locations list. This grouping may automatically create rules in the connectivity server that allow each user in the users list to have access to each location in the locations list.

Figure 2:
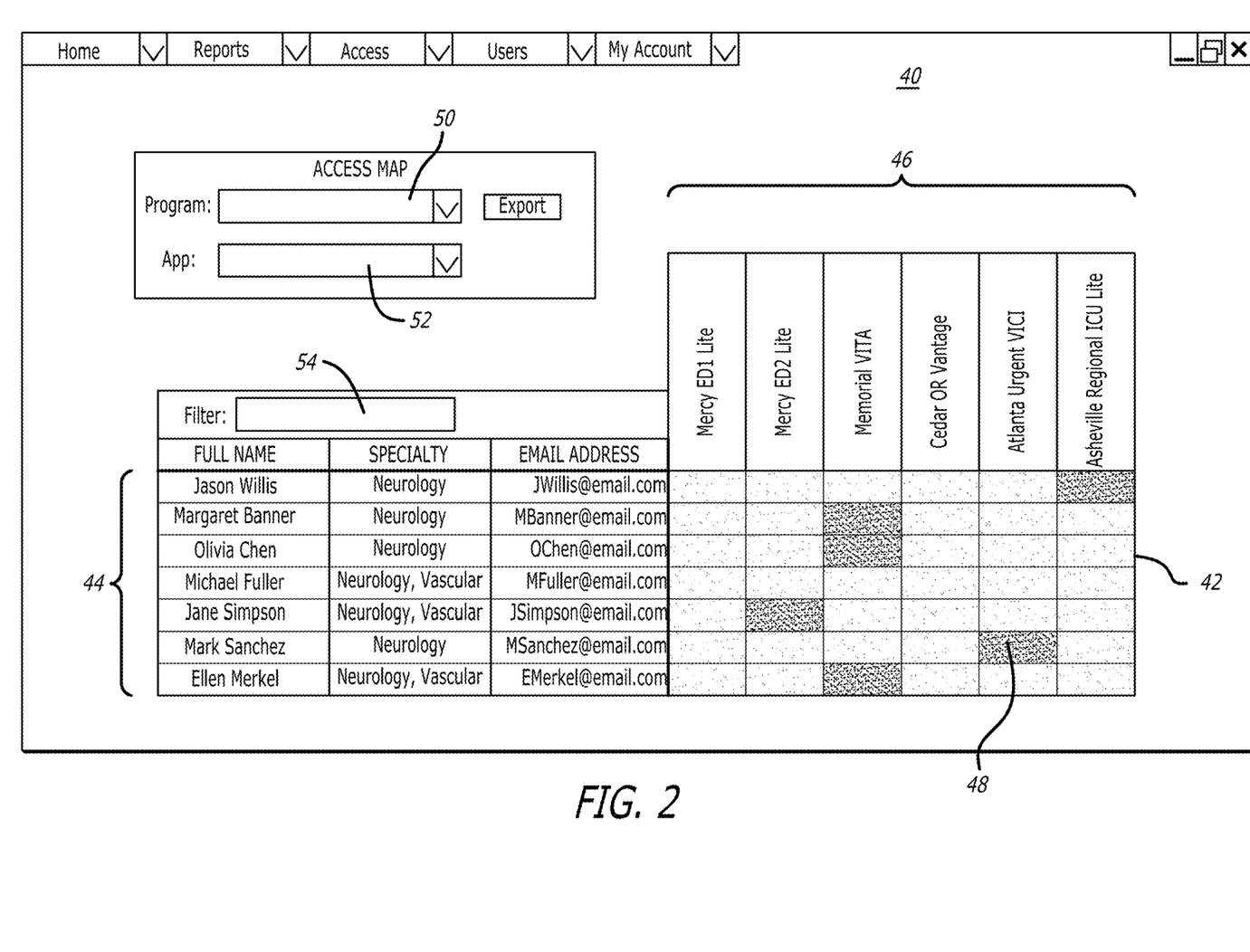
FIG. 2 illustrates an exemplary interactive access map.

The connectivity server 30 may provide a graphical user interface 40 that includes an interactive access map for each program. FIG. 2 shows an example of an interactive access map 42 for a stroke program associated with a Mercy General hospital. The map includes a vertical list 44 of the names and specialties of users on the left that have been added to the users list of the Mercy General stroke program. The map 42 also includes a horizontal list 46 of locations that have been added to the locations list of the Mercy General stroke program. By default, every user in the users list 44 of a program may have access to every location in the locations list 46 of that program. However, in one embodiment, the access map may allow access between specific users and locations to be toggled. For example, as shown in FIG. 2, connectivity is enabled for all of the tiles (each representing a combination of a user and a location) filled gray. However, connectivity has been disabled at one location for each user, as illustrated by the tiles filled black 48. An administrator may toggle connectivity for any user-location combination by clicking on the corresponding tile. The system may also allow the administrator to toggle the connectivity of several users and locations at once using a "CTRL-click" input on various tiles or dragging and highlighting a group of contiguous tiles using a mouse or keyboard input.

The administrator may select different access maps by selecting different programs from the drop-down menu 50 labelled "Program" in the upper-left corner of the interface. The interface may also include another drop-down menu 52 labelled "App" in the upper-left corner that allows the administrator to view access among users and locations across different applications, such as access to remote presence (e.g., two-way audiovisual sessions), access to clinical documentation tools, and/or access to medical records or imagery. The access map may additionally include a filter function 54 to allow the administrator to filter the list of user or locations to find specific users or locations more easily.

The monitoring server 32 maintains a database 56 of status information from each of the patient access devices 22-25. The status information may be reported to the monitoring server 32 from the patient access devices 22-25 periodically, in response to polling by the monitoring server, or in response to an event. Exemplary status information may include detailed device status information, including battery life, LAN ID and connection status, wireless signal strength, whether the device is coupled to a charging station and/or AC power, software version, date and time of last reboot, and other device-related information. The monitoring server 32 also maintains a record of all communications sessions between a patient access device and a provider access device, including the patient access device location and/or device ID, the provider username or ID, the duration of the session, the quality of the session, and other session-related information.

All or a portion of the database 38 of connectivity rules maintained in the connectivity server 30 is mirrored in one or more of the communication servers 26, 28. When a user or care provider wishes to connect to a patient access 22-25 device to conduct a session with a patient, he or she launches a provider access software program on his or her provider access device 34, 36. In another embodiment, the provider may simply direct a web browser to a web-based provider access interface. The user supplies login credentials, such as a username and password, which are transmitted to the communications server for authentication, or to a separate authentication server in communication with the communications server. Once the user is authenticated, the communications server sends to the provider access device a list of patient access devices to which the provider is permitted to connect, as well as a status of each of the devices at the corresponding locations. The device statuses may include ready, busy, and/or offline, depending on whether the device is online and available to participate in a communication session, online but in use by another provider, or offline, respectively.

From the displayed list of patient access devices the provider may then select an available patient access device to connect to, after which the provider access device transmits a request to connect to the patient access device to the communications server. The communications server then begins a process to the establish a communication session between the provider access device and the patient access device. The communications server may employ a process such as that described in U.S. Pat. No. 9,160,783, the contents of which are hereby incorporated by reference. In general, the communication server may first attempt to establish a peer-to-peer session between the patient and provider access devices using firewall traversal techniques such as UDP hole punching and/or those described in ICE/STUN/TURN protocols. If a peer-to-peer session cannot be established between the patient and provider access devices, the server may then attempt to establish a session using itself or another TURN server as a media relay server that relays media back and forth between the patient and provider access devices. In addition, the patient and provider access devices may employ a dynamic bandwidth allocation scheme in order to maximize the quality of the audio/video session through changing network conditions. The dynamic bandwidth allocation scheme may include that described in U.S. Pat. No. 9,264,664, the contents of which are hereby incorporated by reference.

The details of each communication session are logged in the monitoring server 32 and made available to a reporting server. The details of each session may include a username or other identification of the provider, the patient access device location, a serial number or identification of the patient access device, the type of patient access device, the duration of the session, whether the provider accessed the patient's medical records, and/or whether the provider accessed the patient's medical imagery. The identification of the provider may itself be associated with additional details about the provider, such as whether the provider is a part of one or more groups of providers or other healthcare organizations, the name of any such group of providers, and/or the provider's medical specialty or specialties. Similarly, each patient access device location may be associated with additional details regarding the patient access device location, such as the owner, custodian, and/or customer associated with the patient access device location, whether the location is associated with one or more hospitals or healthcare organizations, the name of any such the healthcare organizations, the physical location of the patient access device location, one or more service lines or medical specialties the patient access device is assigned to.

The reporting server may be configured to join usage data of providers and/or patient access device locations with details about each to generate interactive dashboards and reports for visualizing various aspects of the utilization of the telehealth platform. Details of this utilization reporting can be found in U.S. Pat. Nos. 8,902,278 and 9,251,313, the contents of which are hereby incorporated by reference.

The monitoring server may be configured to generate reports including patient access devices and their associated device health information for review by a technician at a remote terminal coupled to the PCN. The monitoring server may additionally be configured to analyze the device health data received form the patient access devices and detect an abnormal condition in one or more of the patient access devices. The analysis of the device health data may include artificial intelligence techniques such as unsupervised or supervised machine learning for anomaly detection. When the monitoring server detects an abnormal condition, the monitoring server may generate an alert to a technician identifying the patient access device requiring attention. Alternatively, the monitoring server may attempt to alleviate the abnormal condition by automatically performing a corrective action. In one embodiment, before generating an alert for a technician, the monitoring server may trigger a reboot for a patient access device that has been identified as having an abnormal condition. In some cases, rebooting the patient access device may correct the abnormal condition and alleviate the need for a technician to service the device.

Although the various servers such as the communications servers, monitoring server, connectivity server, and their associated databases may be illustrated or described as being separate devices, it is to be appreciated that any combination of their respective functionalities could be combined or hosted on a single or any number of physical devices coupled to the public communications network.

Additionally, as will be appreciated by one of ordinary skill in the art, principles of the present disclosure may be reflected in a computer program product on a computer-readable storage medium having computer-readable program code embodied in the storage medium, the computer-readable program code executable by a processor. Any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

While certain exemplary embodiments have been described and shown in the accompanying drawings, it is to be understood that such embodiments are merely illustrative and not restrictive on the broader disclosure, and that this disclosure not be limited to the specific constructions and arrangements shown and described, since various other modifications may occur to those ordinarily skilled in the art.

What is claimed is:

1. A telehealth system, comprising:
    a public communications network (PCN);
    a plurality of provider access devices coupled to the PCN;
    a plurality of patient access devices that can be controlled by any of the plurality of provider access devices, the plurality of patient access devices including a first patient access device at a first location coupled to the PCN via a first local area network (LAN) and a first firewall and a second patient access device at a second location coupled to the PCN via a second LAN and a second firewall;
    a monitoring server coupled to the PCN, the monitoring server receives status information from the plurality of patient access devices, wherein the status information includes presence information indicating the availability of the patient access device to participate in a communication session and device status of the patient access device;
    a connectivity server coupled to the PCN, the connectivity server includes a database of connectivity rules, each connectivity rule including an identification of a healthcare provider and a location of patient access device the healthcare provider is authorized to access; and,
    a plurality of geographically dispersed communications servers coupled to the PCN, each of the plurality of communication servers has a network address on the PCN and is configured to establish a two-way audio/video communication session between one of the provider access devices and one of the patient access devices, wherein,
    at least one of the plurality of communications servers receives and maintains at least a portion of the database of connectivity rules from the connectivity server;
    the first communication firewall and the second communication firewall are configured to allow incoming communications from the network addresses of at least one of the plurality of communication servers;
    the provider access device transmits the identification of a healthcare provider to the communications server and receives from the communications server a list of patient access device locations that the healthcare provider is authorized to access and a status of each patient access device at each of the received locations;
    the provider access device receives a selection of a patient access device location from the healthcare provider and communicates the selected location to an optimal one of the plurality of communications servers, wherein the optimal one of the plurality of communication servers is chosen based on at least one of server proximity, server load, and network conditions;
    the optimal communications server establishes a communication session between the provider access device and the patient access device at the selected location; and,
    the monitoring server stores information regarding the established communication session in a reporting database.

2. The system of claim 1, wherein the system includes at least two geographically dispersed communications servers coupled to the PCN, and a first communications server acts as a master communications server and a second communications server acts as a proxy communications server between the master communications server and one of the provider access device and the patient access device.

3. The system of claim 2, wherein the second communications becomes the master communications server when the first communications server fails.

4. The system of claim 1, wherein the monitoring server generates a prioritized list of patient access devices based on the respective health metrics of the patient access devices.

5. The system of claim 1, wherein the connectivity server generates an interactive connectivity map based on the plurality of connectivity rules.

6. The system of claim 5, wherein interactive connectivity map can be displayed and edited by an administrator from a remote terminal coupled to the PCN.

7. The system of claim 6, wherein the interactive connectivity map includes a first axis including identifications of a plurality of medical providers and a second axis including identifications of patient access device locations.

8. The system of claim 7, wherein the identification of at least one of the plurality of healthcare provider is associated with an identification of a group of healthcare providers.

9. The system of claim 8, wherein the medical provider axis of the interactive connectivity map can be filtered based on the associated group of healthcare providers.

10. The system of claim 7, wherein the identification of at least one of the plurality of patient access device locations is associated with an identification of a healthcare organization.

11. The system of claim 10, wherein the patient access device location axis of the interactive connectivity map can be filtered based on the associated healthcare organization.

12. The system of claim 1, wherein the one or more device health metrics includes at least one of battery life, LAN connection status, wireless network strength, cellular network connection status, device location, time of last device reboot, whether the device is connected to a charging station, whether the device is coupled to AC power, and/or software version.

13. The system of claim 12, wherein the monitoring server is configured to detect an abnormal condition of a patient access device.

14. The system of claim 13, wherein the monitoring server is configured to trigger a reboot of the patient access device in response to detecting the abnormal condition.

15. The system of claim 13, wherein the monitoring server is configured to alert a technician in response to detecting the abnormal condition.

16. The system of claim 1, wherein the patient access device periodically transmits a message to the communications server when the patient access device is not in a communication session.

17. The system of claim 16, wherein the patient access device transmits the message to the communications server in response to a message sent from the communications server.

* * * * *